(12) United States Patent
Du et al.

(10) Patent No.: US 10,551,638 B2
(45) Date of Patent: Feb. 4, 2020

(54) IMAGING APPARATUS AND IMAGING METHOD

(71) Applicant: Beijing Zhigu Rui Tuo Tech Co., Ltd, Beijing (CN)

(72) Inventors: Lin Du, Beijing (CN); Hongjiang Zhang, Beijing (CN)

(73) Assignee: BEIJING ZHIGU RUI TUO TECH CO., LTD., Beijing (CN)

( * ) Notice: Subject to any disclaimer, the term of this patent is extended or adjusted under 35 U.S.C. 154(b) by 0 days.

(21) Appl. No.: 14/781,578

(22) PCT Filed: Dec. 4, 2013

(86) PCT No.: PCT/CN2013/088547
§ 371 (c)(1),
(2) Date: Sep. 30, 2015

(87) PCT Pub. No.: WO2015/014059
PCT Pub. Date: Feb. 5, 2015

(65) Prior Publication Data
US 2016/0139433 A1    May 19, 2016

(30) Foreign Application Priority Data
Jul. 31, 2013    (CN) .......................... 2013 1 0328739

(51) Int. Cl.
*G02C 11/00* (2006.01)
*A61B 3/00* (2006.01)
(Continued)

(52) U.S. Cl.
CPC ............ *G02C 11/10* (2013.01); *A61B 3/0025* (2013.01); *A61B 3/103* (2013.01); *G02C 7/083* (2013.01)

(58) Field of Classification Search
CPC ........ G02C 7/025; G02C 7/024; G02C 11/10; G02B 2027/014; G02B 2027/0178; G02B 2027/0127; G06T 7/0044
(Continued)

(56) References Cited

U.S. PATENT DOCUMENTS

| 4,264,154 A | 4/1981 | Petersen |
| 4,572,616 A | 2/1986 | Kowel et al. |

(Continued)

FOREIGN PATENT DOCUMENTS

| CN | 1372650 | 10/2002 |
| CN | 1470227 | 1/2004 |

(Continued)

OTHER PUBLICATIONS

International Search report dated Jun. 12, 2014 for PCT Application No. PCT/CN2013/088554, 4 pages.
(Continued)

*Primary Examiner* — Stephone B Allen
*Assistant Examiner* — Rahman Abdur
(74) *Attorney, Agent, or Firm* — Amin, Turocy & Watson, LLP

(57) ABSTRACT

An imaging apparatus includes: an imaging lens module, having an adjustable imaging parameter, and used to image an observed object of an imaging receiver; an information processing module, used to detect a focus position of the imaging receiver, and determine the imaging parameter of the imaging lens module according to the focus position; and a lens adjustment module, used to adjust the imaging lens module according to the determined imaging parameter. Through the apparatus and method of the embodiments of the present invention, a focus position of an imaging receiver is automatically detected and an imaging parameter of an imaging lens module located between the imaging
(Continued)

US 10,551,638 B2

Page 2 receiver and an object is automatically adjusted according to the focus position, thereby enabling an imaging receiver (for example, a user's eyes) to conveniently obtain clear imaging of objects at different distances.

26 Claims, 13 Drawing Sheets

(51) Int. Cl.
*A61B 3/103* (2006.01)
*G02C 7/08* (2006.01)

(58) Field of Classification Search
USPC .................................................. 351/158, 205
See application file for complete search history.

(56) References Cited

U.S. PATENT DOCUMENTS

| | | | |
|---|---|---|---|
| 4,973,149 A | 11/1990 | Hutchinson | |
| 5,182,585 A | 1/1993 | Stoner | |
| 5,537,163 A | 7/1996 | Ueno | |
| 6,038,080 A * | 3/2000 | Schachar | G02B 3/14 359/666 |
| 6,072,443 A | 6/2000 | Nasserbakht et al. | |
| 6,111,597 A | 8/2000 | Tabata | |
| 6,151,061 A | 11/2000 | Tokuhashi | |
| 6,152,563 A | 11/2000 | Hutchison et al. | |
| 6,325,513 B1 | 12/2001 | Bergner et al. | |
| 7,001,020 B2 | 2/2006 | Yancey et al. | |
| 7,298,414 B2 | 11/2007 | Stavely et al. | |
| 7,334,892 B2 | 2/2008 | Goodall et al. | |
| 7,486,988 B2 | 2/2009 | Goodall et al. | |
| 7,764,433 B2 | 7/2010 | Kam et al. | |
| 7,766,479 B2 | 8/2010 | Ebisawa | |
| 8,104,892 B2 | 1/2012 | Hillis et al. | |
| 8,109,632 B2 | 2/2012 | Hillis et al. | |
| 8,282,212 B2 | 10/2012 | Hillis et al. | |
| 8,384,999 B1 | 2/2013 | Crosby et al. | |
| 8,896,632 B2 | 11/2014 | MacDougall et al. | |
| 2002/0101568 A1 | 8/2002 | Eberl et al. | |
| 2002/0113943 A1 | 8/2002 | Trajkovic et al. | |
| 2003/0043303 A1 | 3/2003 | Karuta et al. | |
| 2003/0125638 A1 | 7/2003 | Husar et al. | |
| 2005/0003043 A1 | 1/2005 | Sewal et al. | |
| 2005/0014092 A1 | 1/2005 | Hasegawa et al. | |
| 2005/0030438 A1 | 2/2005 | Nishioka | |
| 2006/0016459 A1 | 1/2006 | Mcfarlane et al. | |
| 2006/0103808 A1 | 5/2006 | Horie | |
| 2006/0122530 A1 | 6/2006 | Goodall et al. | |
| 2006/0146281 A1 * | 7/2006 | Goodall | G02B 3/14 351/159.02 |
| 2006/0164593 A1 | 7/2006 | Peyghambarian et al. | |
| 2006/0122531 A1 | 8/2006 | Goodall et al. | |
| 2007/0019157 A1 | 1/2007 | Hills et al. | |
| 2007/0211207 A1 | 9/2007 | Lo et al. | |
| 2008/0002262 A1 | 1/2008 | Chirieleison | |
| 2008/0106633 A1 | 5/2008 | Blum et al. | |
| 2009/0066915 A1 * | 3/2009 | Lai | A61B 3/0285 351/216 |
| 2009/0189974 A1 | 7/2009 | Deering | |
| 2009/0279046 A1 | 11/2009 | Dreher et al. | |
| 2009/0303212 A1 | 12/2009 | Akutsu et al. | |
| 2010/0053539 A1 * | 3/2010 | Lin | G02F 1/13 349/200 |
| 2011/0018903 A1 | 1/2011 | Lapstun et al. | |
| 2011/0019258 A1 | 1/2011 | Levola | |
| 2011/0213462 A1 | 1/2011 | Holladay | |
| 2011/0051087 A1 * | 3/2011 | Inoue | A61B 3/12 351/206 |
| 2011/0199202 A1 | 8/2011 | De Mers et al. | |
| 2011/0242277 A1 | 10/2011 | Do et al. | |
| 2011/0279277 A1 | 11/2011 | Li-Chung | |
| 2012/0007959 A1 | 1/2012 | Kwon et al. | |
| 2012/0013389 A1 | 1/2012 | Thomas et al. | |
| 2012/0038549 A1 | 2/2012 | Mandella et al. | |
| 2012/0092618 A1 * | 4/2012 | Yoo | A61B 3/113 351/209 |
| 2012/0113235 A1 | 5/2012 | Shintani | |
| 2012/0127062 A1 | 5/2012 | Bar-Zeev et al. | |
| 2012/0127422 A1 | 5/2012 | Tian et al. | |
| 2012/0133891 A1 | 5/2012 | Jiang | |
| 2012/0140044 A1 | 6/2012 | Galstian et al. | |
| 2012/0154277 A1 | 6/2012 | Bar-Zeev et al. | |
| 2012/0169730 A1 | 7/2012 | Inoue | |
| 2012/0206485 A1 | 8/2012 | Osterhout et al. | |
| 2012/0212499 A1 | 8/2012 | Haddick et al. | |
| 2012/0212508 A1 | 8/2012 | Kimball | |
| 2012/0242698 A1 | 9/2012 | Haddick et al. | |
| 2012/0290401 A1 | 11/2012 | Neven | |
| 2012/0293773 A1 | 11/2012 | Publicover et al. | |
| 2012/0307208 A1 | 12/2012 | Trousdale | |
| 2013/0044042 A1 | 2/2013 | Olsson et al. | |
| 2013/0050432 A1 | 2/2013 | Perez et al. | |
| 2013/0050646 A1 | 2/2013 | Nanbara | |
| 2013/0072828 A1 | 3/2013 | Sweis et al. | |
| 2013/0093997 A1 | 4/2013 | Utsunomiya et al. | |
| 2013/0107066 A1 | 5/2013 | Venkatraman et al. | |
| 2013/0127980 A1 * | 5/2013 | Haddick | G06F 3/013 348/14.08 |
| 2013/0135203 A1 * | 5/2013 | Croughwell, III | G06F 1/1626 345/158 |
| 2013/0147836 A1 | 6/2013 | Small et al. | |
| 2013/0194323 A1 | 8/2013 | Choi et al. | |
| 2013/0215504 A1 | 8/2013 | Kim et al. | |
| 2013/0241805 A1 | 9/2013 | Gomez | |
| 2013/0241927 A1 | 9/2013 | Vardi | |
| 2013/0278631 A1 | 10/2013 | Border et al. | |
| 2013/0335301 A1 | 12/2013 | Wong et al. | |
| 2013/0335404 A1 | 12/2013 | Westerinen et al. | |
| 2013/0335833 A1 | 12/2013 | Liao et al. | |
| 2013/0342572 A1 | 12/2013 | Poulos et al. | |
| 2014/0078175 A1 | 3/2014 | Forutanpour et al. | |
| 2014/0160157 A1 | 6/2014 | Poulos et al. | |
| 2014/0225915 A1 | 8/2014 | Theimer et al. | |
| 2014/0225918 A1 | 8/2014 | Mittal et al. | |
| 2014/0232746 A1 | 8/2014 | Ro et al. | |
| 2014/0240351 A1 | 8/2014 | Scavezze et al. | |
| 2014/0267400 A1 | 9/2014 | Mabbutt et al. | |
| 2014/0267420 A1 | 9/2014 | Schowengerdt et al. | |
| 2014/0282224 A1 * | 9/2014 | Pedley | G06F 3/017 715/784 |
| 2014/0327875 A1 | 11/2014 | Blum et al. | |
| 2014/0354514 A1 | 12/2014 | Kronsson | |
| 2014/0375680 A1 | 12/2014 | Ackerman et al. | |
| 2015/0002542 A1 | 1/2015 | Chan et al. | |
| 2015/0035861 A1 | 2/2015 | Salter et al. | |
| 2015/0234184 A1 | 8/2015 | Schowengerdt et al. | |
| 2015/0235427 A1 | 8/2015 | Nobori et al. | |
| 2015/0235632 A1 | 8/2015 | Liu et al. | |
| 2015/0070391 A1 | 9/2015 | Nishimaki et al. | |
| 2016/0034032 A1 | 2/2016 | Jeong | |
| 2016/0035139 A1 | 2/2016 | Fuchs et al. | |
| 2016/0062454 A1 | 3/2016 | Wang et al. | |
| 2016/0171772 A1 | 6/2016 | Ryznar et al. | |
| 2016/0189432 A1 | 6/2016 | Bar-Zeev et al. | |
| 2016/0196603 A1 | 7/2016 | Perez et al. | |
| 2016/0299360 A1 | 10/2016 | Fonte et al. | |
| 2016/0370605 A1 | 12/2016 | Ain-Kedem | |
| 2017/0092235 A1 | 3/2017 | Osman et al. | |

FOREIGN PATENT DOCUMENTS

| | | |
|---|---|---|
| CN | 1141602 | 3/2004 |
| CN | 1527126 | 9/2004 |
| CN | 1604014 | 4/2005 |
| CN | 1645244 A | 7/2005 |
| CN | 1653374 | 8/2005 |
| CN | 1901833 | 1/2007 |
| CN | 1912672 A | 2/2007 |
| CN | 2868183 | 2/2007 |
| CN | 1951314 | 4/2007 |

(56) References Cited

FOREIGN PATENT DOCUMENTS

| | | |
|---|---|---|
| CN | 101069106 | 11/2007 |
| CN | 101072534 | 11/2007 |
| CN | 101097293 | 1/2008 |
| CN | 101103902 | 1/2008 |
| CN | 201005945 | 1/2008 |
| CN | 101116609 | 2/2008 |
| CN | 101155258 | 4/2008 |
| CN | 101194198 A | 6/2008 |
| CN | 101430429 | 5/2009 |
| CN | 201360319 | 9/2009 |
| CN | 201352278 | 11/2009 |
| CN | 101662696 | 3/2010 |
| CN | 201464738 | 5/2010 |
| CN | 101782685 | 7/2010 |
| CN | 101819331 | 9/2010 |
| CN | 101819334 | 9/2010 |
| CN | 201637953 | 11/2010 |
| CN | 101900927 A | 12/2010 |
| CN | 101917638 | 12/2010 |
| CN | 201754203 | 3/2011 |
| CN | 102008288 | 4/2011 |
| CN | 102083390 | 6/2011 |
| CN | 102203850 | 9/2011 |
| CN | 102292017 | 12/2011 |
| CN | 102419631 | 4/2012 |
| CN | 102481097 | 5/2012 |
| CN | 101149254 | 6/2012 |
| CN | 102487393 | 6/2012 |
| CN | 202267785 | 6/2012 |
| CN | 102572483 | 7/2012 |
| CN | 102576154 | 7/2012 |
| CN | 202383380 | 8/2012 |
| CN | 102918444 | 2/2013 |
| CN | 102939557 | 2/2013 |
| CN | 102981270 | 3/2013 |
| CN | 103054695 | 4/2013 |
| CN | 103065605 | 4/2013 |
| CN | 103150013 | 6/2013 |
| CN | 103190883 | 7/2013 |
| CN | 103197757 | 7/2013 |
| CN | 103280175 | 9/2013 |
| CN | 103297735 | 9/2013 |
| CN | 103353663 | 10/2013 |
| CN | 103353667 | 10/2013 |
| CN | 103353677 | 10/2013 |
| CN | 103558909 | 2/2014 |
| DE | 19959379 | 7/2000 |
| EP | 2646859 A1 | 10/2013 |
| JP | 03023431 | 1/1991 |
| JP | 2676870 | 11/1997 |
| JP | H09289973 | 11/1997 |
| JP | 3383228 | 3/2003 |
| JP | 2003307466 | 10/2003 |
| JP | 2005058399 | 3/2005 |
| JP | 2007129587 | 5/2007 |
| JP | 201143876 | 3/2011 |
| JP | 2012199621 | 10/2012 |
| JP | 2012247449 | 12/2012 |
| TW | 201012448 | 4/2010 |
| WO | 2004023167 | 3/2004 |
| WO | 2005077258 | 8/2005 |
| WO | 2012075218 | 6/2012 |
| WO | 2012083415 | 6/2012 |
| WO | 2013074851 | 5/2013 |

OTHER PUBLICATIONS

International Search Report dated Jan. 8, 2015 for PCT Application No. PCT/CN2014/088242, 2 pages.
International Search Report dated May 5, 2014 for PCT Application No. PCT/CN20131088544, 4 pages.
International Search Report dated Jun. 5, 2014 for PCT Application No. PCT1CN20131088549, 4 pages.
Smith, et al., "Determining Driver Visual Attention With One Camera", IEEE Transactions on Intelligent Transportation Systems, vol. 4, No. 4, December 2003, 14 Pages.
Singh, et al., "Human Eye Tracking and Related Issues: A Review", International Journal of Scientific and Research Publications, vol. 2, Issue 9, Sep. 2012, ISSN 2250-3153, 9 pages.
Ji et al., "Real-Time Eye, Gaze and Face Pose Tracking for Monitoring Driver Vigilance", Real-Time Imaging 8, 357-377 (2002) available online at http://www.idealibrary.com, 21 pages.
International Search Report dated Mar. 6, 2014 for PCT Application No. PCT/CN2013/088540, 8 pages.
International Search Report dated May 28, 2014 for PCT Application No. PCT/CN2013/088545, 4 pages.
International Search Report dated Apr. 3, 2014 for PCT Application No. PCT/CN2013/088531, 10 pages.
International Search Report dated Feb. 27, 2014 for PCT Application No. PCT/CN2013/088522, 6 pages.
International Search Report dated May 28, 2014 for PCT Application No. PCT/CN2013/088553, 6 pages.
International Search Report dated May 8, 2014 for PCT Application No. PCT/CN2013/088547, 4 pages.
Kim, et al. "A 200 s Processing Time Smart Image Sensor for an Eye Tracker using pixel-level analog image processing", IEEE Journal of Solid-State Circuits, vol. 44, No. 9, Sep. 2009, 10 pages.
Hansen, et al. "In the eye of the beholder: a survey of models for eyes and gaze", IEEE Transactions on Pattern Analysis and Machine Intelligence, vol. 32, No. 3, Mar. 2010, 23 pages.
Office Action dated Jun. 29, 2017 for U.S. Appl. No. 14/783,495, 50 pages.
Dthce Action dated Jun. 29, 2017 for U.S. Appl. No. 14/783,503, 120 pages.
Gao et al. "Measuring Directionality of the Retinal Reflection with a Shack-Hartmann Wavefront Sensor", Dec. 2009, Optics Express, vol. 17, No. 25, Optical Society of America, 20 pages.
Office Action dated Jul. 12, 2017 for U.S. Appl. No. 14/780,519, 45 pages.
Office Action dated Jun. 8, 2017 for U.S. Appl. No. 14/779,968, 79 pages.
Office Action dated May 3, 2017 for U.S. Appl. No. 14/781,306, 46 pages.
Office Action dated Feb. 27, 2017 for U.S. Appl. No. 14/783,495, 39 pages.
Office Action dated Apr. 21, 2017 for U.S. Appl. No. 14/781,581, 19 pages.
Office Action dated Dec. 29, 2016 for U.S. Appl. No. 14/780,519, 25 pages.
Office Action dated Mar. 30, 2017 for U.S. Appl. No. 15/028,019, 36 pages.
Office Action dated Oct. 4, 2017 for U.S. Appl. No. 14/781,584, 95 pages.
Office Action dated Dec. 19, 2017 for U.S. Appl. No. 14/783,503, 78 pages.
Office Action dated Nov. 9, 2017 for U.S. Appl. No. 14/780,519, 24 pages.
Office Action dated Nov. 17, 2017 for U.S. Appl. No. 14/783,495, 32 pages.
Office Action dated Dec. 14, 2017 for U.S. Appl. No. 14/779,321, 82 pages.
Office Action dated Dec. 15, 2017 for U.S. Appl. No. 14/779,968, 67 pages.
Lee et al. "A Robust Eye Gaze Tracking Method Based on a Virtual Eyeball Model", Machine Vision and Applications, (2009) 20:319-337, Springer-Verlag, 2008. 19 pages.
Office Action dated Feb. 5, 2018 for U.S. Appl. No. 14/779,321, 38 pages.
Notice of Allowance dated Sep. 11, 2018 for U.S. Appl. No. 14/780,519, 29 pages.
Office Action dated Jun. 25, 2018 for U.S. Appl. No. 14/779,321, 43 pages.
Office Action dated Jun. 14, 2018 for U.S. Appl. No. 14/780,519, 29 pages.
Office Action dated Jul. 13, 2018 for U.S. Appl. No. 14/783,495, 36 pages.

(56) References Cited

OTHER PUBLICATIONS

Office Action dated Jul. 17, 2018 for U.S. Appl. No. 14/781,584, 75 pages.
Office Action dated Sep. 20, 2018 for U.S. Appl. No. 14/779,968, 71 pages.
Notice of Allowance dated Apr. 17, 2019 for U.S. Appl. No. 14/783,495, 23 pages.
Office Action dated Apr. 25, 2019 for U.S. Appl. No. 14/779,968, 70 pages.
Office Action dated May 2, 2019 for U.S. Appl. No. 14/781,584, 105 pages.
Jeong et al., "Tunable microdoublet lens array", Optics Express, vol. 12, Issue 11, May 31, 2004, pp. 2494-2500.
Beauchemin et al., "The Computation of Optical Flow", ACM Computing Surveys, vol. 27, No. 3, Sep. 1995, pp. 433-467.
Notice of Allowance dated Nov. 20, 2018 for U.S. Appl. No. 14/779,321, 31 pages.
Office Action dated Dec. 21, 2018 for U.S. Appl. No. 14/783,495, 35 pages.

\* cited by examiner

Detect a focus position of an imaging receiver, and determine an imaging parameter of an imaging lens module according to the focus position, where the imaging lens module is located between the imaging receiver and an observed object and has an adjustable imaging parameter — S110

Adjust the imaging lens module according to the determined imaging parameter — S120

IMAGING APPARATUS AND IMAGING METHOD

RELATED APPLICATIONS

This application is a U.S. National Stage filing under 35 U.S.C. § 371 of international patent cooperation treaty (PCT) application No. PCT/CN2013/088547, filed Dec. 4, 2013, and entitled "IMAGING APPARATUS AND IMAGING METHOD," which claims priority to Chinese Patent Application No. 201310328739.0, filed with the Chinese Patent Office on Jul. 31, 2013 and entitled "IMAGING APPARATUS AND METHOD", which applications are hereby incorporated herein by reference in their respective entireties.

TECHNICAL FIELD

The present application relates to the field of imaging technologies, and more particularly to an imaging apparatus and method.

BACKGROUND

Wearable devices such as Google glass and smartwatches are gradually accepted by people, and these electronic smart devices will make people's life more and more convenient.

Conventional myopia glasses or hyperopia glasses add a concave lens or a convex lens with a fixed focal length before the eye of a person that suffers from a refractive error to correct various refractive error problems of different causes. However, conventional glasses have the troubles of optometry and lens fitting, and can only solve problems such as correction within a certain distance range. For an object beyond a certain distance, a user may be unable to obtain a clear image and has an indistinct vision, or sees the object with a difficulty that the eyes get tired easily.

Based on the foregoing case, multi-focus glasses with each lens having a plurality of different focal lengths appear. By using an example in which glasses are worn for eyes with both presbyopia and myopia, the upper portion of the glass is a myopia lens and is used to help a user to see an object at a far place clearly; the lower portion of the glass is a hyperopia lens and is used to help a user to see an object at a near place clearly. However, the user needs to see a far place through the upper portion of the glass while see a near place through the lower portion; for example, the user needs to lower the head to see an object that is low at a far place and raise the head to see a object that is high at a near place; or the user needs to manually adjust the position of the glasses, which makes the use troublesome.

Similarly, healthy human eyes and an imaging recording apparatus such as a camera or a video recorder also cannot obtain clear images of objects at all distances within a visual field. For example, when healthy human eyes see an object very close to the eyes, the eyes may also see the object unclearly or get tired.

A lens and a lens array with an electronically adjustable focal length are conventionally known, where the focal length of a lens can be adjusted. However, adaptive adjustment of the focal length of a lens after automatic detection of the focus of a user's eyes is not mentioned.

SUMMARY

A technical problem to be solved by one or more embodiments of the present application is to provide an imaging apparatus and method, so as to automatically adjust an imaging parameter of an imaging apparatus according to a focus of an imaging receiver, thereby enabling the imaging receiver (for example, a user's eyes) to conveniently obtain clear imaging of objects at different distances, thereby improving user experience.

To achieve the foregoing objective, in a first aspect, the present application provides an imaging apparatus, which includes:

an imaging lens module, having at least one adjustable imaging parameter, and used to image an observed object of an imaging receiver;

an information processing module, used to detect a focus position of the imaging receiver, and determine the imaging parameter of the imaging lens module according to the focus position; and a lens adjustment module, used to adjust the imaging lens module according to the determined imaging parameter.

In a second aspect, the present application further provides an imaging method, which includes:

detecting a focus position of an imaging receiver, and determining at least one imaging parameter of an imaging lens module according to the focus position, where the imaging lens module is located between the imaging receiver and an observed object, and the imaging parameter is adjustable; and adjusting the imaging lens module according to the determined imaging parameter.

In the technical solutions of the embodiments of the present application, a focus position of an imaging receiver is automatically detected and an imaging parameter of an imaging lens module located between the imaging receiver and an object is automatically adjusted according to the focus position, thereby enabling an imaging receiver (for example, a user's eyes) to conveniently obtain clear imaging of objects at different distances.

Particularly, for a user's eyes that suffers from a problem such as a refractive error, the apparatus and method of the embodiments of the present application may solve the problems, such as indistinct vision and eye exhaustion caused by insufficient (when myopic eyes see an object at a far place, or hyperopic eyes see an object at a near place) or excessive (myopic eyes see an object at a near place, or hyperopic eyes see an object at a far place) refractive correction, that occur in watching objects at different distances; problems of indistinct vision and eyes exhaustion caused by decreased lens adjustment range when presbyopic eyes see objects at a near place and at a far place at the same time; and problems of indistinct vision and eyes exhaustion caused by optical axis offsets from astigmatism and strabismus.

BRIEF DESCRIPTION OF THE DRAWINGS

The present disclosure will become more fully understood from the detailed description given herein below for illustration only, and thus are not limitative of the present disclosure, and wherein.

DETAILED DESCRIPTION

The method and apparatus of the present application are illustrated below in detail with reference to the accompanying drawings and embodiments.

An imaging receiver has a limited adjustment range of an imaging parameter such as a focal length. By using an example that the imaging receiver is a user's eyes (definitely, the imaging receiver may further be an imaging recording apparatus such as a video recorder and a camera), a user with a normal eyesight may be unable to see, or sees with a great difficulty, an object very close to the eyes. The adjustment range is limited further for eyes that have problems such as refractive errors such as myopia, hyperopia, presbyopia, and astigmatism and strabismus. By using presbyopic eyes that are not normal for both near vision and far vision as an example, to see an object clearly, the eyes often stay in an adjustment state, which easily causes eye exhaustion. Although common glasses can be worn for correction, glasses in the prior art can hardly perform imaging correction for objects at both a far place and a near place.

Figure 1:
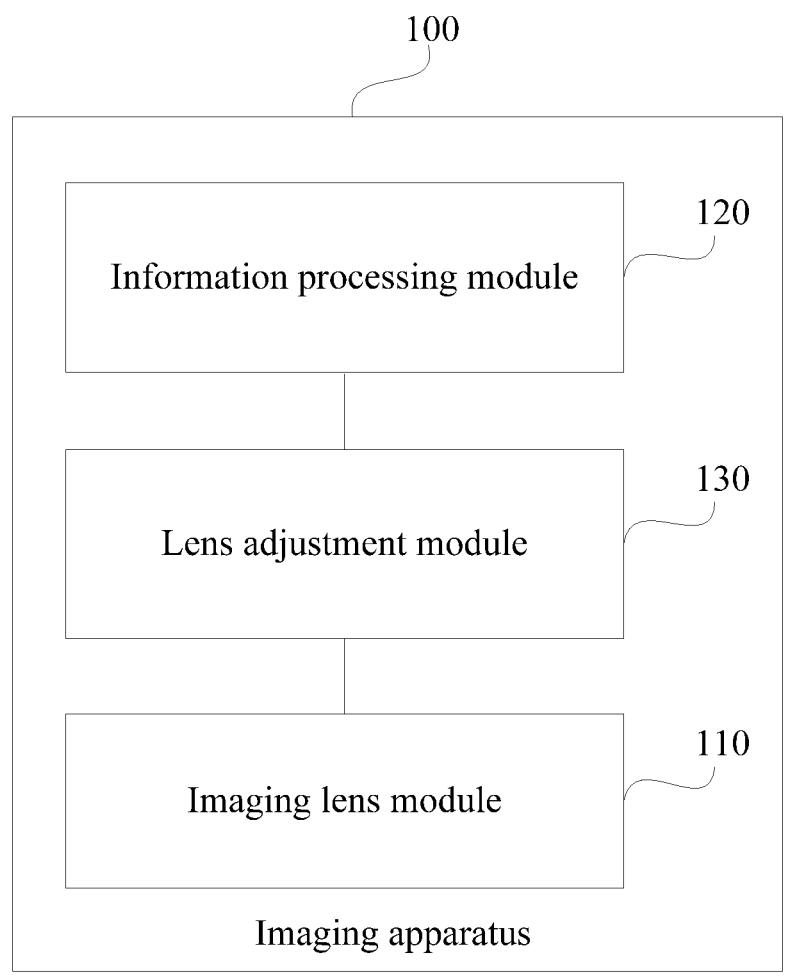
FIG. 1 is a schematic structural block diagram of an imaging apparatus according to an embodiment of the present application.

Therefore, as shown in FIG. 1, an embodiment of the present application provides an imaging apparatus 100, which includes an imaging lens module 110, an information processing module 120, and a lens adjustment module 130.

The imaging lens module 110 has an adjustable imaging parameter and is used to image an observed object of an imaging receiver.

The information processing module 120 is used to detect a focus position of the imaging receiver, and determine the imaging parameter of the imaging lens module according to the focus position.

The lens adjustment module 130 is used to adjust the imaging lens module according to the determined imaging parameter.

The imaging receiver can obtain an expected image of an object with the imaging lens module 110.

The imaging apparatus according to the embodiment of the present application can correspondingly adjust imaging parameters for objects at different distances in a visual field according to a demand of an imaging receiver, thereby enabling a user to comfortably watch the objects at different distances in the visual field, respectively, thereby improving user experience.

Figure 2:
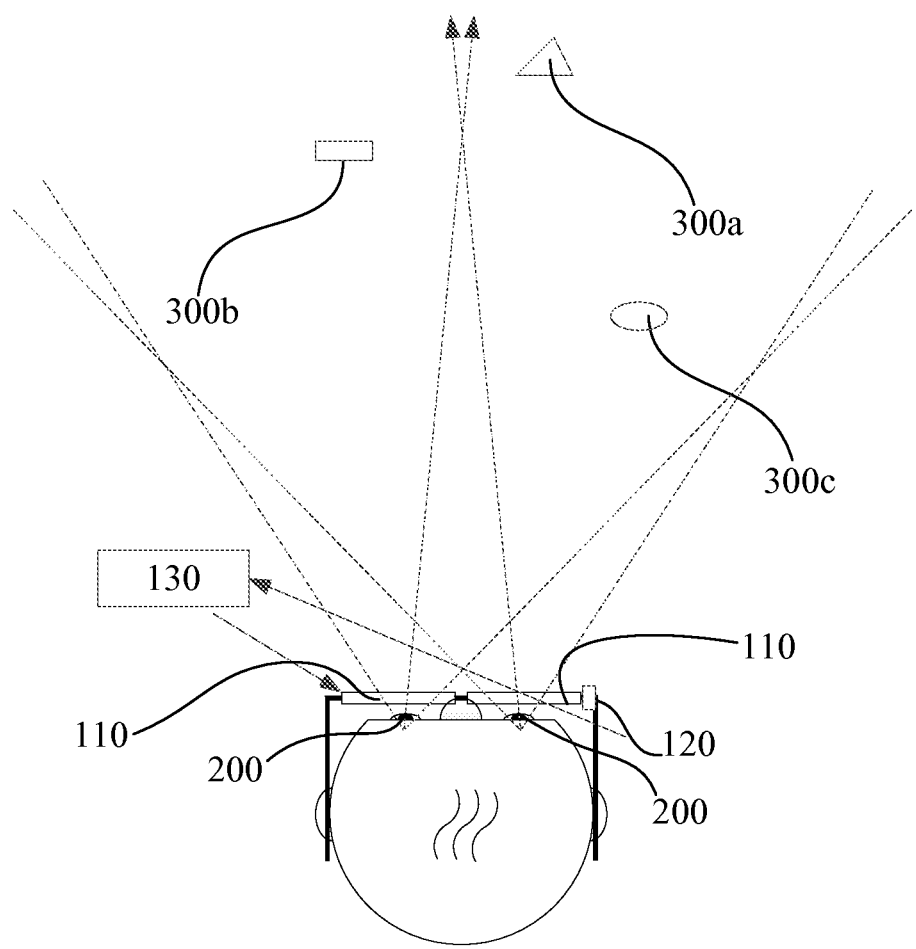
FIG. 2 is a schematic view of an application of an imaging apparatus according to an embodiment of the present application.

As shown in FIG. 2, in an implementation manner of the embodiment of the present application, an example in which the imaging apparatus 100 is glasses (here, except common glasses, the glasses may also be optical devices such as goggles and windshields), an imaging receiver 200 is a user's eyes, and the objects include a triangular object 300a, a rectangular object 300b, and an elliptic object 300c with decreasing distances from the imaging apparatus 100 is used for illustration, where the lens at each side of the glasses is the imaging lens module 110.

In a possible implementation manner of the embodiment of the present application, the imaging lens module 110 includes at least one lens. Here, an example in which each imaging lens module 110 only includes one lens is used for illustration.

In a preferred implementation manner of the embodiment of the present application, the imaging parameter of the imaging lens module 110 includes: a shape and/or a refractive index of the imaging lens module.

In this implementation manner, the adjustment to the imaging parameter of the imaging lens module 110 may be: for example, the curvature of the lens of the imaging lens module 110 is adjusted to change the focal length of the imaging lens module 110; or the refractive index of the lens of the imaging lens module 110 is adjusted to change the focal length of the imaging lens module 110. In addition, for an astigmatic user, the surface of the lens of the imaging lens module 110 can be adjusted to a cylindrical surface to correct astigmatism; for a strabismal user, the surface of the lens of the imaging lens module 110 can be adjusted to a prismatic surface to correct strabismus. Definitely, in other possible implementation manners of the embodiment of the present application, the imaging lens module may further include two or more lenses, and in this case, for an astigmatic or strabismal user, the imaging lens module 110 of one lens is adjusted to a cylindrical surface or a prismatic surface.

Figure 3A:
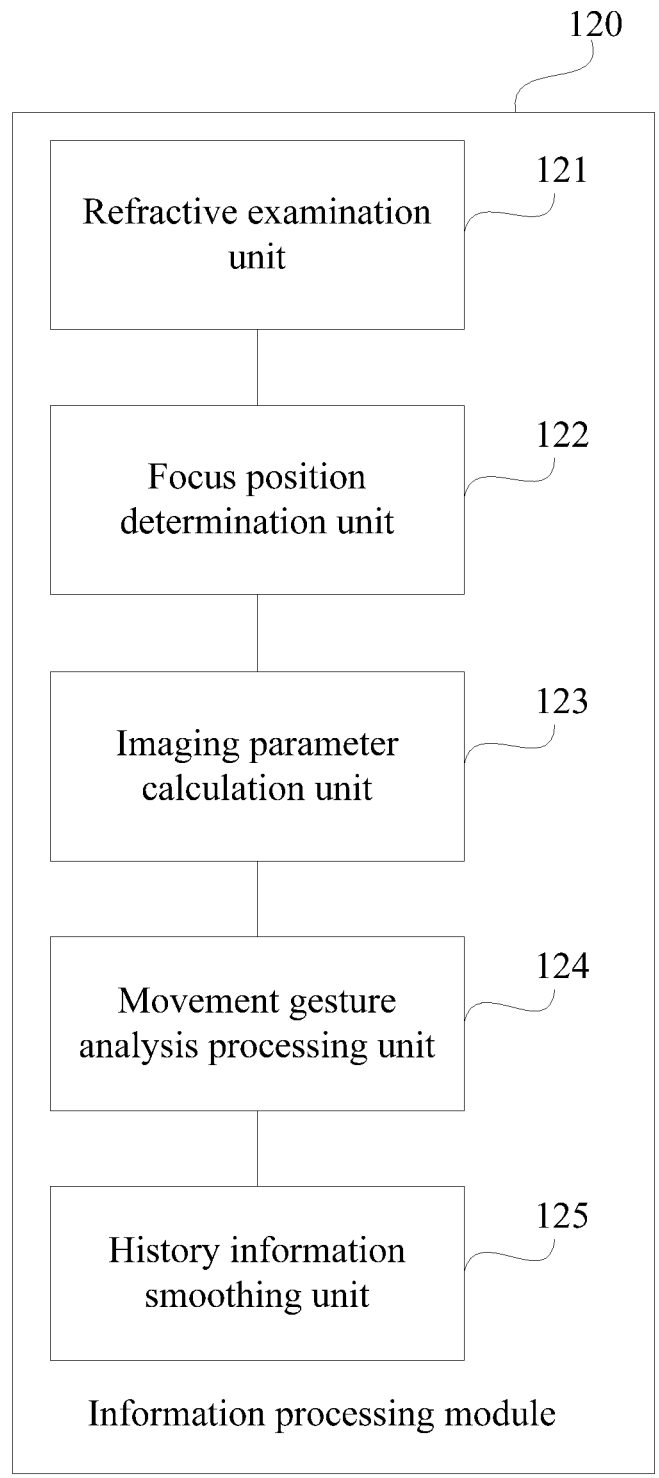
FIG. 3a is a schematic structural block diagram of an information processing module in an imaging apparatus according to an embodiment of the present application.

As shown in FIG. 3a, in a possible implementation manner of the embodiment of the present application, the information processing module 120 includes a refractive examination unit 121, a focus position determination unit 122, an imaging parameter calculation unit 123, and a movement gesture analysis processing unit 124.

The refractive examination unit 121 is used to learn imaging parameters corresponding to the imaging receiver 200 when the imaging receiver 200 acquires expected images of objects at a plurality of distances, and obtain refractive examination information corresponding to the imaging receiver. Here, the expected image may be, for example, a clear image or a relatively clear image of an object. When the imaging receiver 200 is eyes, the expected image here may be a clear or relatively clear image of an object that a user's eyes watch comparatively comfortably, that is, when the user watches the clear image of the object, the eyes do not require excessive adjustment and do not get exhausted easily.

Table 1 shows a representative example of refractive examination information of a myopia user corresponding to the imaging receiver in this embodiment obtained in this implementation manner. Here, the target distance is the distance between an object and an imaging apparatus (in other implementation manners, the distance between an object and the imaging receiver can further be selected as the target distance). The optimal refractivity is the refractivity that a corresponding region of the imaging lens module is required to reach when the user's eyes watch the clear image of the object comfortably at the target distance. In other embodiments of the present application, the refractive examination information may further include, for example, optical parameter information for other refractive errors such as astigmatism or strabismus.

TABLE 1

Representative example of refractive examination information

| | Target distance | | | | | | |
|---|---|---|---|---|---|---|---|
| | 0.1 m | 0.2 m | 0.5 m | 1 m | 10 m | 50 m | 100 m | Infinitely far |
| Optimal refractivity | −0.5 | −2.5 | −5.5 | −5.75 | −6.00 | −6.25 | −6.50 | −6.75 |

For example, it is assumed that the distance between an object and the imaging apparatus is 1 m, and therefore the imaging parameter of the imaging lens module 110 corresponding to the object preferably corresponds to the refractivity −5.75. It is assumed that the distance between an object and the imaging apparatus is 0.8 m, and therefore the optimal refractivity corresponding to the distance of 0.8 m may be obtained through an interpolation method according to the corresponding optimal refractivities of 0.5 m and 1 m, and an imaging parameter of a corresponding imaging lens module 110 is further obtained. A person skilled in the art should know that when the granularity of the distance of the object for learning the imaging parameter corresponding to the imaging receiver is smaller, more refractive examination information is obtained, and the accuracy of the imaging parameter of the required imaging lens module 110 obtained through the refractive examination information is higher.

The focus position determination unit 122 is used to determine a focus position of the imaging receiver according to an optical parameter of the imaging receiver. When the focus position of the imaging receiver is obtained, the distance between the object and the imaging apparatus is obtained.

The imaging parameter calculation unit 123 is used to calculate the imaging parameter of the imaging lens module 110 according to the focus position of the imaging receiver and the refractive examination information corresponding to the imaging receiver. In this implementation manner, the imaging parameter of the corresponding imaging lens module 110 of each object is calculated through the lookup method based on Table 1.

To avoid that when a user moves at a high speed, because an observed object in a visual field keeps changing, timely adjustment fails as the adjustment speed of the imaging apparatus cannot follow the speed that the object changes or the user feels dizzy though timely adjustment succeeds, preferably, in a possible implementation manner of the embodiment of the present application, the information processing module 120 further includes a movement gesture analysis processing unit 124.

The movement gesture analysis processing unit 124 is used to determine the imaging parameter of the imaging lens module 110 according to movement gesture information of the imaging apparatus 100 (or the imaging lens module 110).

Here, the movement gesture information of the imaging apparatus includes: the relative movement gesture information of the imaging apparatus and the object and/or the movement speed information of the imaging apparatus.

Figure 3B:
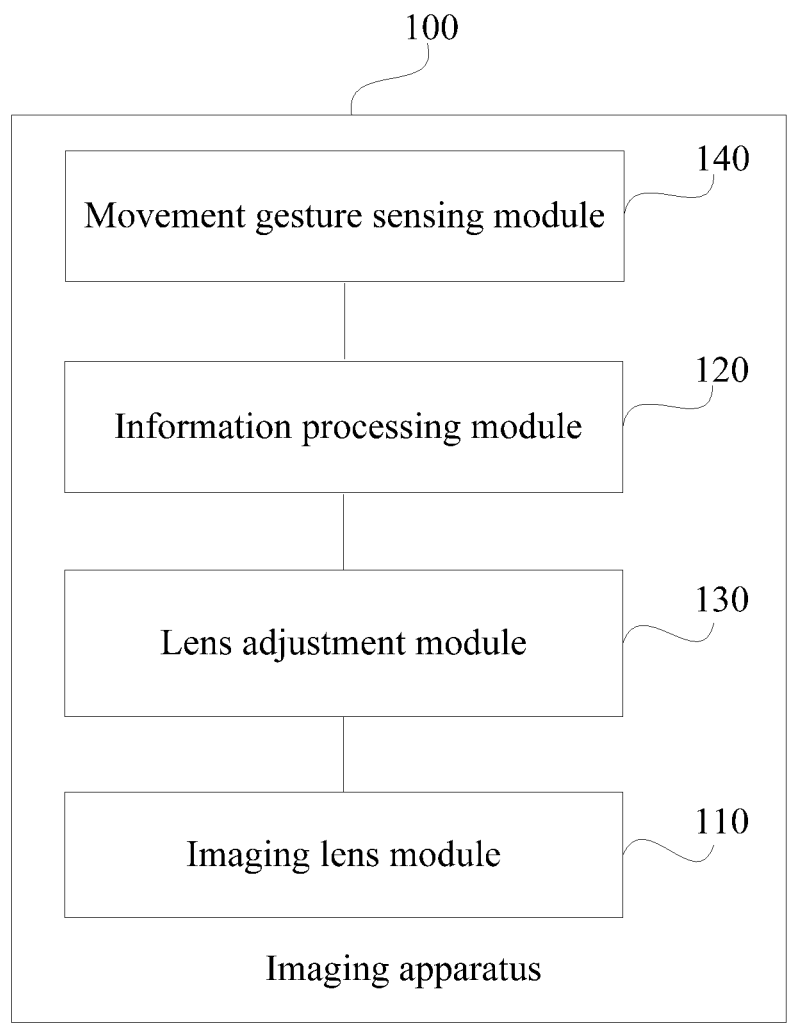
FIG. 3b is a schematic structural block diagram of another imaging apparatus according to an embodiment of the present application.

Preferably, in this implementation manner, as shown in FIG. 3b, the movement gesture information of the imaging apparatus can be acquired by adding a movement gesture sensing module 140 in the imaging apparatus.

Figure 3C:
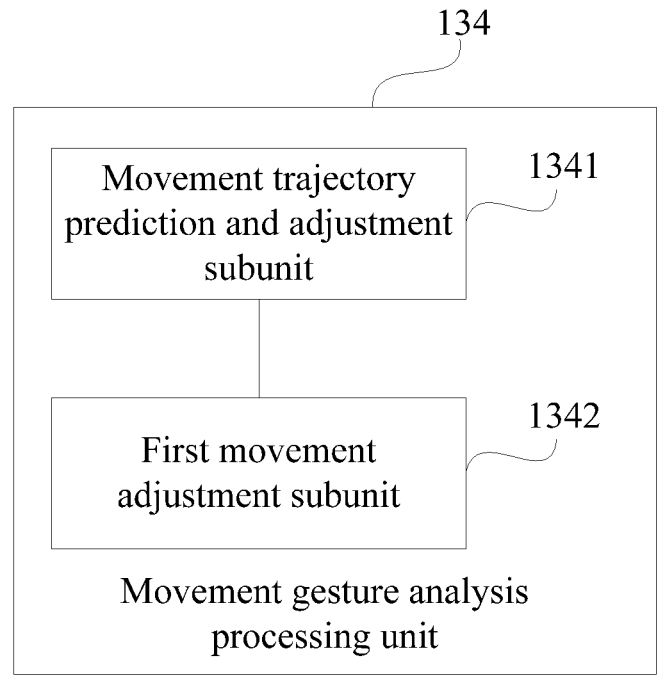
FIG. 3c and FIG. 3d are schematic structural block diagrams of a movement gesture analysis processing unit in an imaging apparatus according to an embodiment of the present application.
Figure 3D:
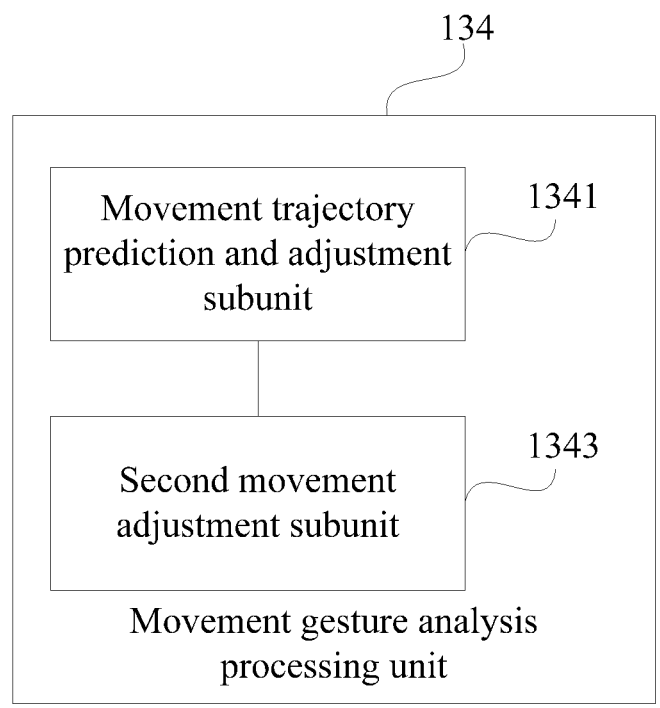

Preferably, as shown in FIG. 3c and FIG. 3d, the movement gesture analysis processing unit 124 includes:

a movement trajectory prediction and adjustment subunit 1241, used to predict the imaging parameter corresponding to the imaging lens module 110 at a next moment according to the relative movement gesture information of the imaging apparatus and the object and the imaging parameter of the imaging lens module at a current moment. For example, the object moves in the direction towards the imaging receiver, and a movement speed is 0.5 m per second, so that the distance between the object and the imaging apparatus at a next second can be predicted according to the current distance between the object and the imaging apparatus and the foregoing information, so as to further adjust the imaging parameter of the imaging lens module 10.

In a possible implementation manner of the embodiment of the present application, preferably, the movement gesture analysis processing unit 124 includes:

a first movement adjustment subunit 1242 or a second movement adjustment subunit 1243, used to, when a movement speed of the imaging apparatus exceeds a set threshold value, adjust the imaging parameter of the imaging lens module to a set common imaging parameter or the value of the imaging parameter of the imaging lens module at a previous moment.

Preferably, in a possible implementation manner of the embodiment of the present application, to prevent hopping in time on the imaging parameter of the imaging lens module 110 which causes a user's dizziness, the information processing module 120 further includes:

a history information smoothing unit 125, used to perform smoothing processing of time on the current imaging parameter of the imaging lens module 110 according to history information of the imaging parameter of the imaging lens module 110.

In a possible implementation manner of the embodiment of the present application, the focus position determination unit can obtain the focus position with three forms of systems:

A first focus position determination unit can obtain the focus position of the imaging receiver according to an imaging parameter of an optical path between an image collection device and an imaging receiver when a clearest image presented on an imaging plane of the imaging receiver is collected (when the imaging receiver is an eye, the imaging plane is the eyeground (for example, a retina) of the eye). The first focus position determination unit is described in further detail below.

Figure 4:
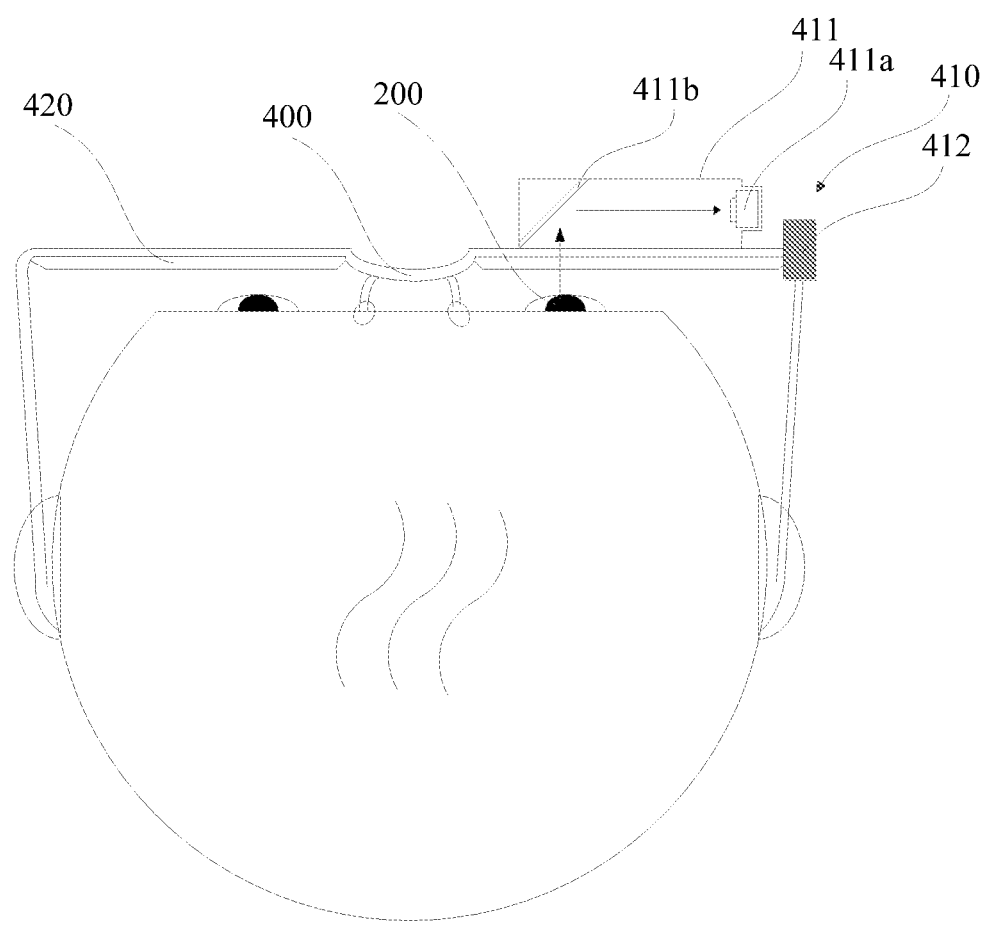
FIG. 4 is a schematic view of an application of yet another imaging apparatus according to an embodiment of the present application.

A second focus position determination unit calculates the focus position of the imaging receiver by tracking an optical axis direction of the imaging receiver with an optical axis tracking system and then obtaining a scenario depth of the position of an observed object with a depth sensing device. FIG. 4 shows an example that the imaging apparatus 400 uses the second focus position determination unit 410 to determine the focus position of the eye 200 (the imaging receiver). As can be seen from FIG. 4, in this implementation manner, the imaging apparatus 400 is glasses. The imaging lens module is a lens 420 of the glasses. A sightline tracker 411 (in this implementation manner, the sightline tracker 411 includes a camera 411a and a beamsplitter 411b for forming an optical path between the eye 200 and the camera 411a; the sightline tracker belongs to the prior art, and is no longer described here) serves as an eye optical axis tracking system to track an optical axis direction of the eye. Also, a depth sensor 412 is used to obtain a scenario depth of the position of the observed object (obtaining a scenario depth with a depth sensor also belongs to the prior art, and is no longer described here). The focus position of the eye is then calculated through a triangular relationship.

A third focus position determination unit is applicable to a scenario where the imaging apparatus corresponds to at least two correlated imaging receivers, tracks optical axis directions of the at least two imaging receivers using an optical axis tracking system, and then obtains focus positions of the imaging receivers through an intersection of the optical axis directions of the at least two imaging receivers. For example, the optical axis directions of the two eyes are tracked respectively, and after the optical axis directions of the two eyes are obtained, the position of the intersection of the two optical axes is calculated, so as to obtain the focus position of the eyes. This implementation manner requires at least two imaging receivers (for example, a human's two eyes) and is not applicable to a scenario where only one imaging receiver exists.

Figure 5A:
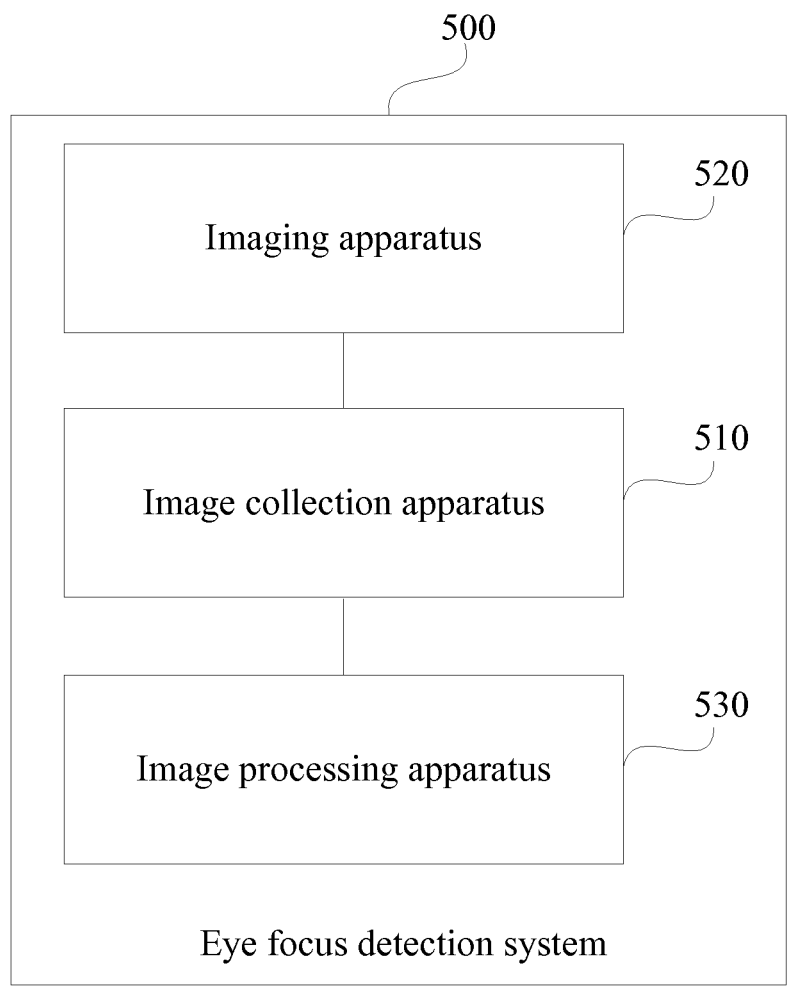
FIG. 5a is a structural block diagram of an eye focus detection system of an imaging apparatus according to an embodiment of the present application.

In a possible implementation manner of the embodiment of the present application, the function of the first focus position determination unit may be implemented by a focus detection system, and an example in which the imaging receiver is an eye is used for illustration below:

As shown in FIG. 5a, an embodiment of the present application provides an eye focus detection system 500, which includes an image collection apparatus 510, an imaging apparatus 520, and an image processing apparatus 530.

The image collection apparatus 510 is used to collect an image presented on an eyeground.

The imaging apparatus 520 is used to adjust an imaging parameter between an eye and the image collection apparatus 510 to enable the image collection apparatus 510 to obtain a clearest image.

The image processing apparatus 530 is used to process the image obtained by the image collection apparatus 510, so as to obtain an optical parameter of the eye when the image collection apparatus obtains the clearest image.

The system 500 performs analysis processing on the image on the eyeground of the eye to obtain an optical parameter of the eye when the image collection apparatus obtains the clearest image, so as to calculate the current focus position of the eye, which provides a basis for further implementing an adaptive operation of the eye.

Here, the image presented on the "eyeground" is mainly an image presented on a retina, which may be an image of the eyeground itself, or may be an image of another object projected on the eyeground. Here, the eyes may be a human's eyes, or may also be other animal's eyes.

Figure 5B:
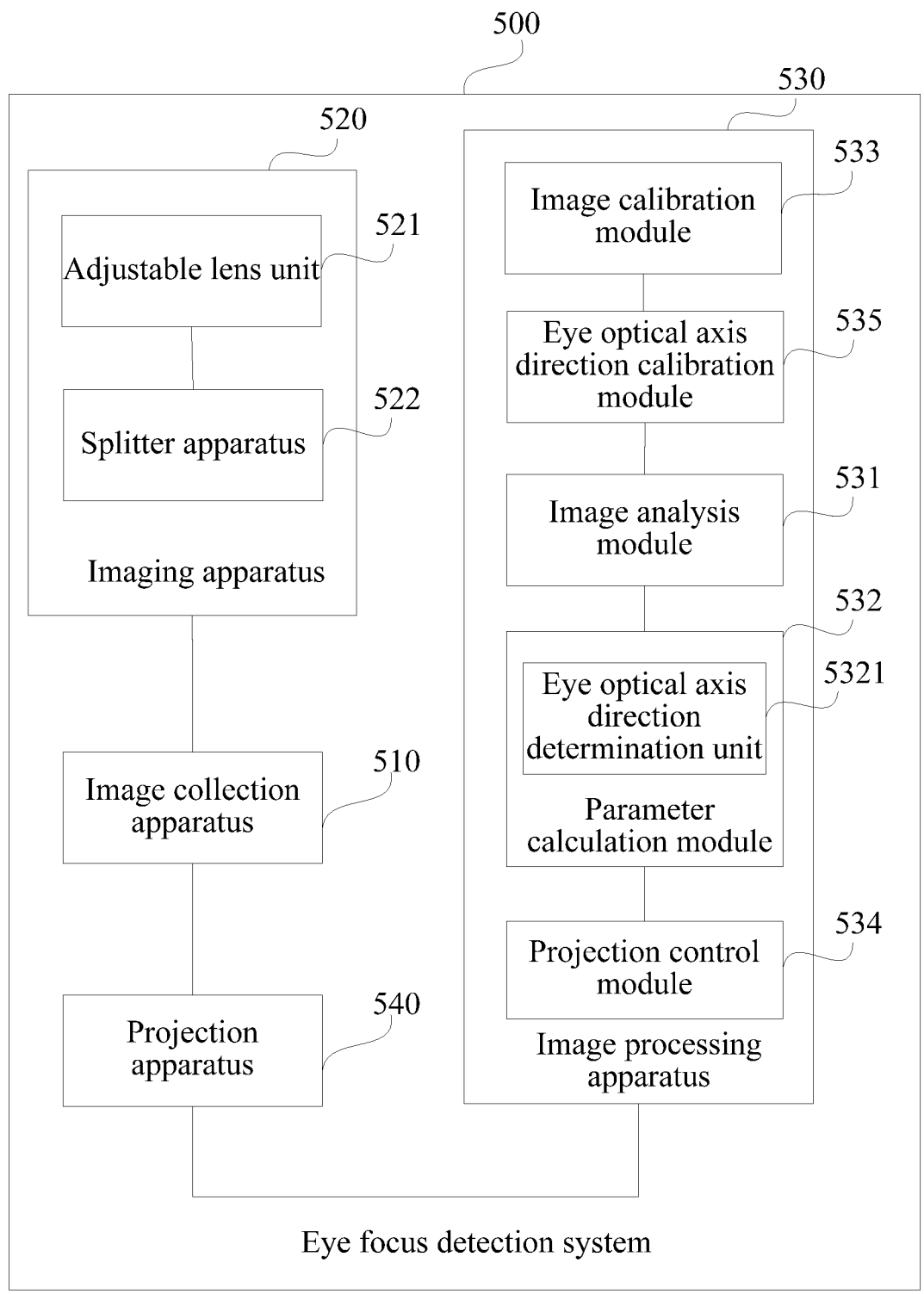
FIG. 5b is a structural block diagram of another eye focus detection system of an imaging apparatus according to an embodiment of the present application.

As shown in FIG. 5b, in a possible implementation manner of the embodiment of the present application, the image collection apparatus 510 is a subminiature camera, and in another possible implementation manners of the embodiment of the present application, the image collection apparatus 510 may further directly use a photosensitive imaging apparatus, an apparatus such as a CCD or CMOS.

In a possible implementation manner of the embodiment of the present application, the imaging apparatus 520 includes: an adjustable lens unit 521, located on an optical path between the eye and the image collection apparatus 510, having an adjustable focal length and/or an adjustable position in the optical path. By means of the adjustable lens unit 521, the system equivalent focal length between the eye and the image collection apparatus 510 becomes adjustable, and with the adjustment of the adjustable lens unit 521, the image collection apparatus 510 can obtain a clearest image on the eyeground at a position or state of the adjustable lens unit 521. In this implementation manner, the adjustable lens unit 521 is adjusted continuously in real time in the detection process.

Preferably, in a possible implementation manner of the embodiment of the present application, the adjustable lens unit 521 is a focal-length adjustable lens, used to adjust a refractive index and/or a shape thereof to accomplish the adjustment of the focal length thereof. Specifically: 1) The focal length is adjusted through adjusting the curvature of at least one surface of the focal-length adjustable lens; for example, the curvature of the focal-length adjustable lens is adjusted by increasing or reducing a liquid medium in a cavity formed by double transparent layers. 2) The focal length is adjusted through changing the refractive index of the focal-length adjustable lens; for example, a specific liquid crystal medium is filled in the focal-length adjustable lens, and the arrangement manner of the liquid crystal medium is adjusted through adjusting the voltage of a corresponding electrode of the liquid crystal medium, so as to change the refractive index of the focal-length adjustable lens.

In another possible implementation manner of the embodiment of the present application, the adjustable lens unit 521 includes: a lens group, used to adjust relative positions of lenses in the lens group to accomplish the adjustment of the focal length of the lens group.

In addition to the foregoing two manners of changing an optical path parameter of a system through adjusting the characteristic of the adjustable lens unit 521, the optical path parameter of the system can further be changed through adjusting the position of the adjustable lens unit 521 on the optical path.

Preferably, in a possible implementation manner of the embodiment of the present application, to prevent the watching experience of an observed object from being affected for a user, and to apply the system on a wearable device portably, the imaging apparatus 520 further includes: a splitter apparatus 522, used to form optical transfer paths between the eye and the observed object and between the eye and the image collection apparatus 510. Therefore, the optical path can be folded, thereby decreasing the volume of the system, and also minimize other experience for the user.

Preferably, in this implementation manner, the splitter apparatus includes: a first splitter unit, located between the eye and the observed object, and used to transmit light from the observed object to the eye, and transfer light from the eye to the image collection apparatus.

The first splitter unit may be a beamsplitter, a splitter light waveguide (including an optical fiber) or other suitable splitter devices.

In a possible implementation manner of the embodiment of the present application, the image processing apparatus 530 of the system includes an optical path calibration module, used to calibrate the optical path of the system, for example, calibrate the alignment of optical axes of optical paths, so as to ensure the precision of measurement.

In a possible implementation manner of the embodiment of the present application, the image processing apparatus 530 includes:

an image analysis module 531, used to analyze the image obtained by the image collection apparatus to find the clearest image; and a parameter calculation module 532, used to calculate the optical parameter of the eye according to the clearest image and the imaging parameter of the system known when the clearest image is obtained.

In this implementation manner, by means of the imaging apparatus 520, the image collection apparatus 510 can obtain the clearest image. However, the image analysis module 531 needs to find the clearest image. At this time, the optical parameter of the eye can be calculated according to the clearest image and the known optical path parameter of the system. Here, the optical parameter of the eye may include the optical axis direction of the eye.

In a possible implementation manner of the embodiment of the present application, preferably, the system further includes: a projection apparatus 540, used to project a light spot to the eyeground. In a possible implementation manner, the function of the projection apparatus may be implemented by a miniature projector.

Here, the projected light spot may have no specific pattern and is only used to illuminate the eyeground.

Figure 5C:
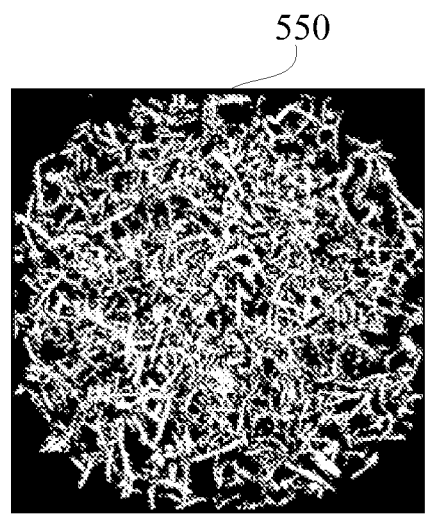
FIG. 5c is a schematic view of a light spot pattern used by an eye focus detection system of an imaging apparatus according to an embodiment of the present application.
Figure 5D:
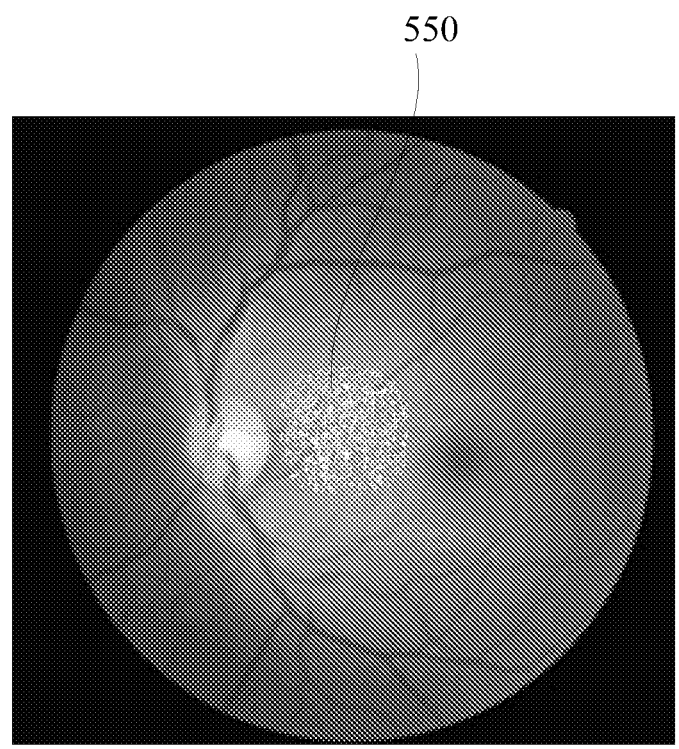
FIG. 5d is a schematic view of an image on an eyeground having a light spot pattern photographed by an eye focus detection system of an imaging apparatus according to an embodiment of the present application.

In a preferable implementation manner of the embodiment of the present application, the projected light spot includes a pattern rich in features. The rich features of the pattern can facilitate detection and increase the precision of detection. FIG. 5c shows an exemplary view of a light spot pattern 550, and the pattern may be formed by a light spot pattern generator, for example, ground glass. FIG. 5d shows the image on the eyeground photographed when there is a projection of the light spot pattern 550.

To prevent normal watching of eyes from being affected, preferably, the light spot is an infrared light spot invisible to eyes.

At this time, to reduce interferences of other spectrums:

A transmission filter for light invisible to eyes may be disposed on an exit surface of the projection apparatus.

A transmission filter for light invisible to eyes may be disposed on an incident surface of the image collection apparatus.

Preferably, in a possible implementation manner of the embodiment of the present application, the image processing apparatus 530 further includes:

a projection control module 534, used to control the brightness of a projected light spot of the projection apparatus according to the result obtained by the image analysis module.

For example, the projection control module 534 can adaptively adjust the brightness according to the characteristic of the image obtained by the image collection apparatus 510. Here, the characteristic of the image includes the contrast of the image feature, the texture feature, and the like.

Here, a special case of controlling the brightness of the projected light spot of the projection apparatus is to turn on or off the projection apparatus. For example, when a user continuously stares at a point, the projection apparatus may be turned off periodically. When the user's eyeground is bright enough, the light emitting source may be turned off and only the eyeground information is used to detect the distance between the current sightline focus of the eye and the eye.

In addition, the projection control module 534 can further control the brightness of the projected light spot of the projection apparatus according to ambient light.

Preferably, in a possible implementation manner of the embodiment of the present application, the image processing apparatus 530 further includes: an image calibration module 533, used to calibrate an image on an eyeground, so as to obtain at least one reference image corresponding to an image presented on an eyeground.

The image analysis module 531 can perform comparison and calculation on the image obtained by the image collection apparatus 530 and the reference image, so as to obtain the clearest image. Here, the clearest image may be an obtained image having minimum differences from the reference image. In this implementation manner, a difference between the current obtained image and the reference image can be calculated through an existing image processing algorithm, for example, by using a classic automatic focusing algorithm for a phase difference value.

Preferably, in a possible implementation manner of the embodiment of the present application, the parameter calculation module 532 includes:

an eye optical axis direction determination unit 5321, used to obtain the optical axis direction of the eye according to the feature of the eye when the clearest image is obtained.

Here, the feature of the eye may be acquired from the clearest image, or may also be acquired in other manners. The optical axis direction of the eye represents the stared direction of the eye's sightline.

Preferably, in a possible implementation manner of the embodiment of the present application, the eye optical axis direction determination unit 5321 includes: a first determination subunit, used to obtain the optical axis direction of the eye according to the feature of the eyeground when the clearest image is obtained. Compared with obtaining the optical axis direction of an eye through features of a pupil and an eyeball surface, determining the optical axis direction of an eye through the feature of the eyeground has higher precision.

When a light spot pattern is projected to the eyeground, the size of the light spot pattern may be greater than an eyeground visible region or smaller than an eyeground visible region, in which:

when the area of the light spot pattern is smaller than or equal to that of the eyeground visible region, the optical axis direction of the eye can be determined through detecting the position of the light spot pattern on the image relative to the eyeground by using a classic feature point matching algorithm (for example, a Scale Invariant Feature Transform (SIFT) algorithm)); and when the area of the light spot pattern is greater than or equal to that of the eyeground visible region, the direction of the user's sightline can be determined by determining the optical axis direction of the eye through the obtained position of the light spot pattern on the image relative to the original light spot pattern (obtained by the image calibration module).

In another possible implementation manner of the embodiment of the present application, the eye optical axis direction determination unit 5321 included: a second determination subunit, used to obtain the optical axis direction of the eye according to the feature of the pupil of the eye when the clearest image is obtained. Here, the feature of the pupil of the eye may be acquired from the clearest image, or may also be acquired in other manners. The obtaining the optical axis direction of the eye through the feature of the pupil of the eye belongs to the prior art, which is no longer described here.

Preferably, in a possible implementation manner of the embodiment of the present application, the image processing apparatus 530 further includes: an eye optical axis direction calibration module 535, used to calibrate the optical axis direction of the eye, so as to determine the optical axis direction of the eye more precisely.

In this implementation manner, the known imaging parameter of the system includes a fixed imaging parameter and a real-time imaging parameter, where the real-time imaging parameter is the parameter information of the adjustable lens unit when the clearest image is acquired, and the parameter information may be recorded in real time when the clearest image is acquired.

Figure 5E:
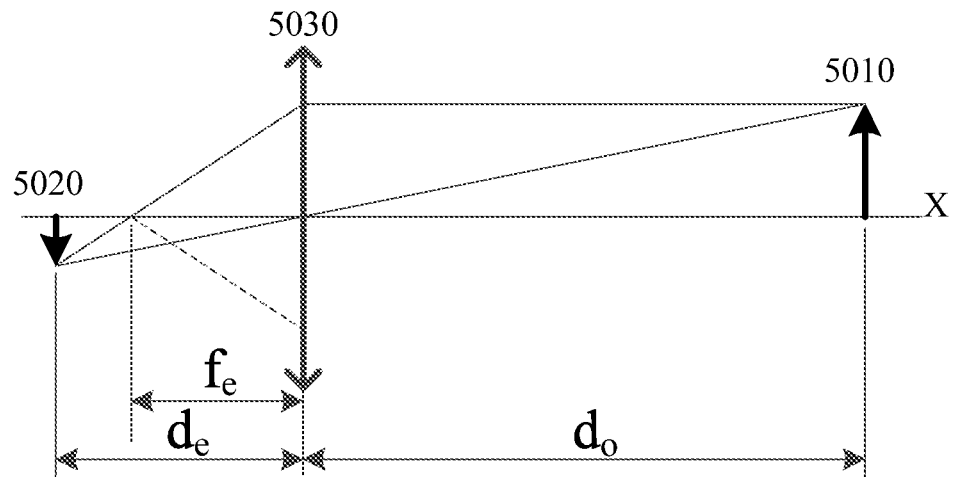
FIG. 5e is a schematic view of an optical path for imaging of an eye of an eye focus detection system of an imaging apparatus according to an embodiment of the present application.

After the current optical parameter of the eye is obtained, the distance from the focus of the eye to the eye can be calculated, specifically:

FIG. 5e is a schematic view of imaging of an eye, and by combining a lens imaging formula in the classic optical theory, formula (1) can be obtained from FIG. 5e:

$$\frac{1}{d_o} + \frac{1}{d_e} = \frac{1}{f_e} \quad (1)$$

where $d_o$ and $d_e$ are distances from the current observed object 5010 of the eye and from the real image 5020 on the retina to an eye equivalent lens 5030, respectively, $f_e$ is the equivalent focal length of the eye equivalent lens 5030, and X is the sightline direction of the eye (which can be obtained from the optical axis direction of the eye).

Figure 5F:
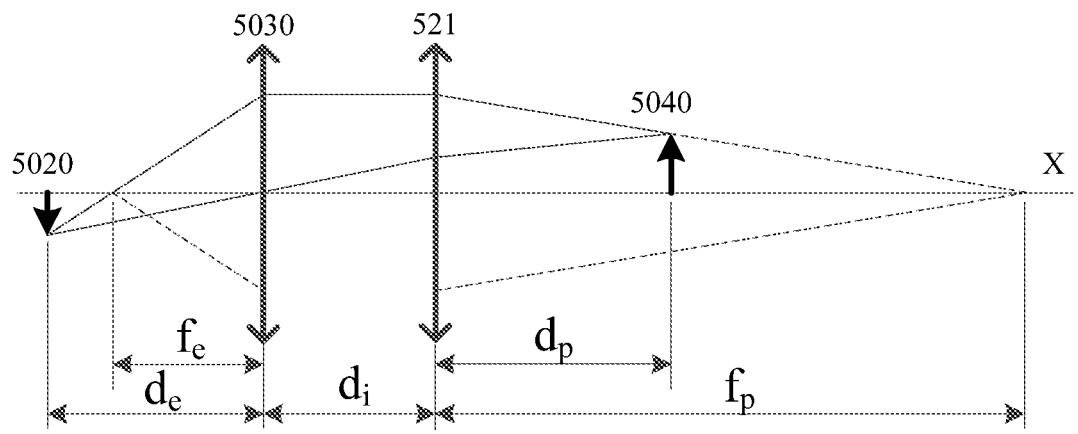
FIG. 5f is a schematic view of a distance from the focus of an eye to the eye obtained by an eye focus detection system of an imaging apparatus according to a known imaging parameter of the system and an optical parameter of the eye according to an embodiment of the present application.

FIG. 5f is a schematic view of obtaining a distance from the focus of an eye to the eye according to a known imaging parameter of a system and the optical parameter of the eye. The light spot 5040 in FIG. 5f turns into a virtual image (not shown in FIG. 5f) through the adjustable lens unit 521, and it is assumed that the distance from the virtual image to the lens is x (not shown in FIG. 5f), the following equation group can be obtained by combining formula (1):

$$\begin{cases} \frac{1}{d_p} - \frac{1}{x} = \frac{1}{f_p} \\ \frac{1}{d_i + x} + \frac{1}{d_e} = \frac{1}{f_e} \end{cases} \quad (2)$$

where $d_p$ is the optical equivalent distance from the light spot 5040 to the adjustable lens unit 521, $d_i$ is the optical equivalent distance from the adjustable lens unit 521 to the eye equivalent lens 5030, $f_p$ is the value of the focal length of the adjustable lens unit 521, and $d_i$ is the distance from the eye equivalent lens 5030 to the adjustable lens unit 521.

The distance $d_o$ from the current observed object 5010 (the focus of the eye) to the eye equivalent lens 5030 can be obtained from (1) and (2), as shown by formula (3):

$$d_o = d_i + \frac{d_p \cdot f_p}{f_p - d_p} \quad (3)$$

According to the calculated distance from the observed object 5010 to the eye, and also the optical axis direction of the eye that can be obtained from the record above, the focus position of the eye can be easily obtained, which provides a basis for subsequent further interactions related to the eye.

Figure 6:
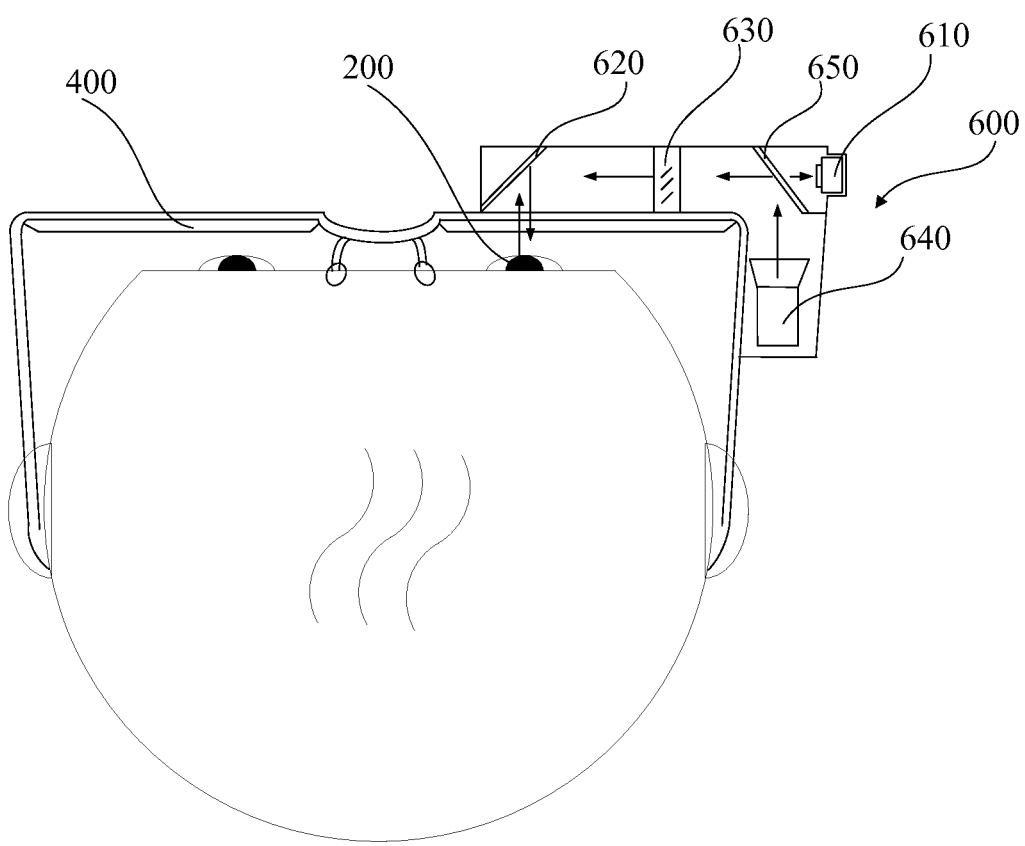
FIG. 6 is a schematic view of an application of an eye focus detection system of an imaging apparatus on glasses according to an embodiment of the present application.

FIG. 6 shows an embodiment that an eye focus detection system 600 of a possible implementation manner of the embodiment of the present application is applied on the glasses 400 (here, the glasses 400 may be an imaging apparatus according to an embodiment of the present application), which includes the content recorded in the implementation manner shown in FIG. 5b. Specifically, as can be seen from FIG. 6, in this implementation manner, the system 600 of this implementation manner is integrated on the right side of the glasses 400 (the present application is not limited thereto), and includes a subminiature camera 610, a first beamsplitter 620, and a focal-length adjustable lens 630.

The subminiature camera 610 has the same effect as the image collection apparatus recorded in the implementation manner in FIG. 5b, and in order not to affect the sightline that the user normally watches an object, the subminiature camera 610 is disposed on the right outer side of the glasses 200.

The first beamsplitter 620 has the same effect as the first splitter unit recorded in the implementation manner in FIG. 5b, and is disposed with a tilt angle at the intersection between the staring direction of the eye 200 and the incident direction of the camera 610, so as to transmit light of the observed object that enters the eye 200 and reflect light from the eye to the camera 610.

The focal-length adjustable lens 630 has the same effect as the focal-length adjustable lens recorded in the implementation manner in FIG. 5b, is located between the first beamsplitter 620 and the camera 610, and adjusts the value of the focal length in real time, so that a value of the focal length, the camera 610 can photograph a clearest image on the eyeground.

In this implementation manner, the image processing apparatus is not shown in FIG. 6, whose function is the same as that of the image processing apparatus shown in FIG. 5b.

The brightness of an eyeground is generally insufficient, and therefore illumination for the eyeground is recommended. In this implementation manner, a light emitting source 640 illuminates the eyeground. In order not to affect the user experience, here the light emitting source 640 is preferably light invisible to eyes, and is preferably a near-infrared light emitting source which does not affect the eye 200 much but the camera 610 is relatively sensitive to.

In this implementation manner, the light emitting source 640 is located at the outer side of the glass frame on the right side, and therefore one second beamsplitter 650 and the first beamsplitter 620 are needed to accomplish together the transfer of light emitted by the light emitting source 640 to the eyeground. In this implementation manner, the second beamsplitter 650 is further located in front of the incident surface of the camera 610, and therefore further needs to transmit light from the eyeground to the second beamsplitter 650.

As can be seen, in this implementation manner, to improve user experience and increase collection clarity of the camera 610, the first beamsplitter 620 preferably has the characteristic a high reflectivity for infrared and high transmittance for visible light. For example, an infrared reflective film may be disposed on the side facing the eye 200 of the first beamsplitter 620 to achieve the characteristic.

As can be seen from FIG. 6, because in this implementation manner, the eye focus detection system 600 is located at a side of the lens of the glasses 600 far from the eye 200, during calculation of the optical parameter of the eye, the lens can be regarded as a part of the eye, and in this case the optical characteristic of the lens does not need to be known.

In other implementation manners of the embodiment of the present application, the eye focus detection system 600 may be located at a side of the lens of the glasses 400 near the eye 200, and in this case, the optical characteristic parameter of the glass needs to be obtained in advance, and during the calculation of the distance from the focus, the influences of the glass need to be considered.

The light emitted by the light emitting source is reflected by the second beamsplitter 650, projected by the focal-length adjustable lens 630, and reflected by the first beamsplitter 620, then enters a user's eyes through the lens of the glasses 400, and eventually reaches a retina of an eyeground. The camera 610 photographs the image on the eyeground through the pupil of eye 200 via the optical path formed by the first beamsplitter 620, the focal-length adjustable lens 630, and the second beamsplitter 650.

Figure 7:
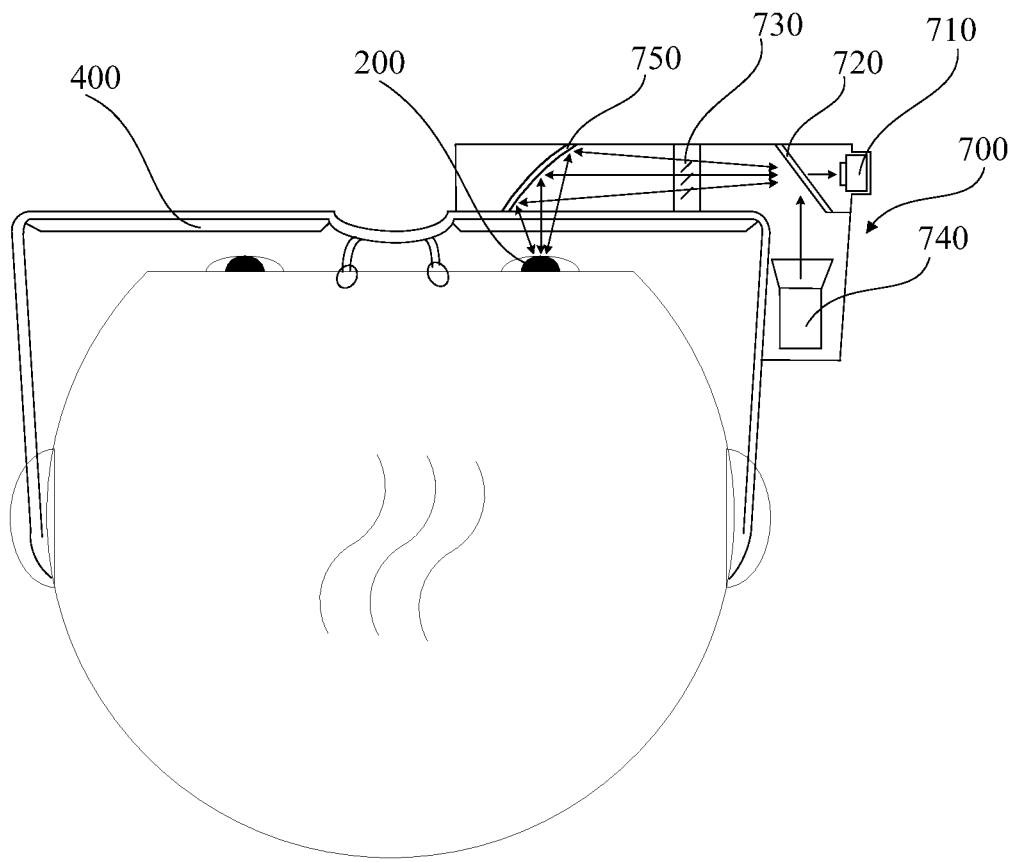
FIG. 7 is a schematic view of an application of an eye focus detection system of another imaging apparatus on glasses according to an embodiment of the present application.

FIG. 7 shows a schematic structural view of an eye focus detection system 700 of another implementation manner according to an embodiment of the present application. As can be seen from FIG. 7, this implementation manner is similar to the implementation manner shown in FIG. 6, and includes a subminiature camera 710, a second beamsplitter 720, and a focal-length adjustable lens 730. The difference lies in that the projection apparatus 740 in this implementation manner is a projection apparatus 740 for projecting a light spot pattern, and a curved surface beamsplitter 750 replaces the first beamsplitter in the implementation manner in FIG. 6.

Here, the curved surface beamsplitter 750 transfers an image presented on an eyeground to the image collection apparatus respectively corresponding to the position of a pupil when the optical axis direction of the eye is different. In this manner, the camera can photograph imaging mixed and interposed from different angles of the eyeball. However, because only the eyeground part of the pupil can be clearly imaged on the camera, other parts are defocused to cause clear imaging to fail, and therefore prevent severe interferences on the imaging of the eyeground part, and the features of the eyeground part can still be detected. Therefore, compared with the implementation manner shown in FIG. 6, this implementation manner can desirably obtain an image on an eyeground when an eye stares at different directions, so that the eye focusing detection apparatus of this implementation manner has a wider application scope and higher precision of detection.

Figures 8, 9:
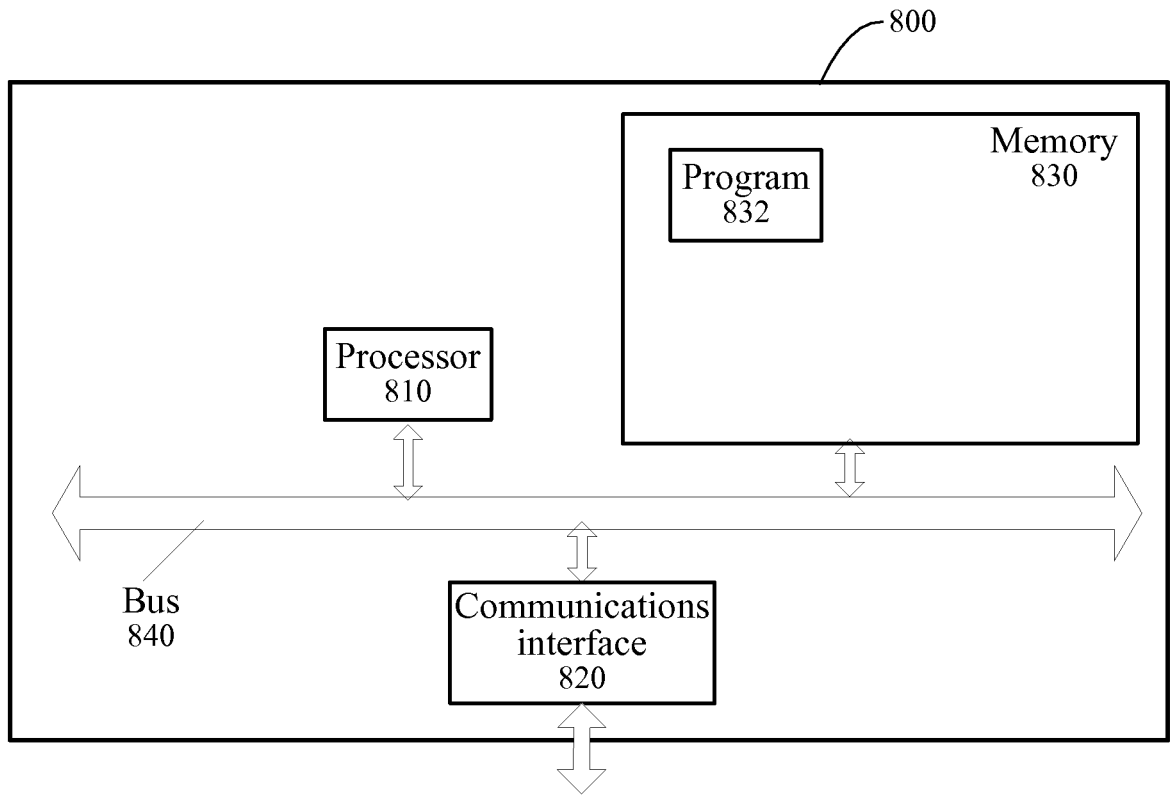
FIG. 8 is a structural block diagram of an information processing module of an imaging apparatus according to an embodiment of the present application.
FIG. 9 is a flow chart of an imaging method according to an embodiment of the present application.

As shown in FIG. 8, in a possible implementation manner of the embodiment of the present application, the information processing module 800 may, for example, include:

a processor 810, a communications interface 820, a memory 830, and a communications bus 840.

The communications among the processor 810, the communications interface 820, and the memory 830 are accomplished through the communications bus 840.

The communications interface 820 is used to perform network element communications.

The processor 810 is used to execute a program 832, and specifically can execute the functions corresponding to the information processing module.

Specifically, the program 832 may include a program code, and the program code includes a computer operation instruction.

The processor 810 may be a central processing unit (CPU), or an application specific integrated circuit (ASIC), or one or more integrated circuits configured to implement the embodiment of the present application.

The memory 830 is used to store the program 832. The memory 830 may contain a high-speed random access memory (RAM) memory, or may also further include a non-volatile memory, for example, at least one disk memory. The program 832 can specifically enable the information processing module 800 to execute the following steps:

learning corresponding imaging parameters when the imaging receiver acquires expected images of objects at a plurality of distances, and obtaining refractive examination information corresponding to the imaging receiver;

determining a focus position of the imaging receiver according to an optical parameter of the imaging receiver; and calculating an imaging parameter of an imaging lens module according to the focus position of the imaging receiver and the refractive examination information corresponding to the imaging receiver.

The specific implementation of the steps in the program 832 can be referred to the corresponding description of corresponding steps and units in the embodiments of the present application, which is no longer elaborated here. A person skilled in the art shall clearly understand that for convenience and simplicity of description, the specific work process of devices and modules described above can be referred to the description of the corresponding process in the foregoing method embodiments, which is no longer elaborated here.

As shown in FIG. 9, an embodiment of the present application proposes an imaging method, which includes:

S110: Detect a focus position of an imaging receiver, and determine an imaging parameter of an imaging lens module according to the focus position, where the imaging lens module is located between the imaging receiver and an observed object and has an adjustable imaging parameter.

S120: Adjust the imaging lens module according to the determined imaging parameter.

Preferably, in a possible implementation manner of the embodiment of the present application, the imaging parameter of the imaging lens module includes: a shape and/or a refractive index of the imaging lens module.

Preferably, in a possible implementation manner of the embodiment of the present application, before the step of determining an imaging parameter of an imaging lens module according to the focus position, the method includes:

learning the corresponding imaging parameters when the imaging receiver acquires expected images of objects at a plurality of distances, respectively, and obtaining refractive examination information corresponding to the imaging receiver.

Preferably, in a possible implementation manner of the embodiment of the present application, Step S110 includes:

determining the focus position of the imaging receiver according to an optical parameter of the imaging receiver; and calculating the imaging parameter of the imaging lens module according to the focus position of the imaging receiver and the refractive examination information corresponding to the imaging receiver.

Preferably, in a possible implementation manner of the embodiment of the present application, the method further includes:

determining the imaging parameter of the imaging lens module according to movement gesture information of the imaging lens module.

Preferably, in a possible implementation manner of the embodiment of the present application, the step of determining the imaging parameter of the imaging lens module according to movement gesture information of the imaging lens module includes:

predicting the imaging parameter of the imaging lens module corresponding to a next moment according to relative movement gesture information of the imaging lens module and an object and the imaging parameter of the imaging lens module at a current moment.

Preferably, in a possible implementation manner of the embodiment of the present application, the step of determining the imaging parameter of the imaging lens module according to movement gesture information of the imaging lens module includes:

when a movement speed of the imaging lens module exceeds a set threshold value, adjusting the imaging parameter of the imaging lens module to a set common imaging parameter.

Preferably, in a possible implementation manner of the embodiment of the present application, the step of determining the imaging parameter of the imaging lens module according to movement gesture information of the imaging lens module includes:

when a movement speed of the imaging lens module exceeds a set threshold value, adjusting the imaging parameter of the imaging lens module to an imaging parameter value of the imaging lens module at a previous moment.

Preferably, in a possible implementation manner of the embodiment of the present application, before the step of determining the imaging parameter of the imaging lens module according to movement gesture information of the imaging lens module, the method further includes:

acquiring the movement gesture information of the imaging lens module.

Preferably, in a possible implementation manner of the embodiment of the present application, the movement gesture information of an imaging apparatus includes: the relative movement gesture information of the imaging lens module and the object and/or movement speed information of the imaging apparatus.

Preferably, in a possible implementation manner of the embodiment of the present application, the method further includes:

Performing smoothing processing of time on a current imaging parameter of the imaging lens module according to history information of the imaging parameter of the imaging lens module.

Preferably, in a possible implementation manner of the embodiment of the present application, the imaging receiver is a user's eyes.

Preferably, in a possible implementation manner of the embodiment of the present application, the imaging apparatus is glasses.

Preferably, in a possible implementation manner of the embodiment of the present application, the step of determining the focus position of the imaging receiver according to an optical parameter of the imaging receiver includes:

obtaining the focus position of the imaging receiver according to an imaging parameter of an optical path between an image collection device and an imaging receiver when a clearest image presented on an imaging plane of the imaging receiver is collected.

Preferably, in a possible implementation manner of the embodiment of the present application, the step of determining the focus position of the imaging receiver according to an optical parameter of the imaging receiver includes:

collecting the image presented on the imaging plane of the imaging receiver;

adjusting the imaging parameter of the optical path between the imaging receiver and the image collection device to collect the clearest image; and processing the collected image, and calculating the focus position of the imaging receiver according to the imaging parameter of the optical path between the image collection device and the imaging receiver and the optical parameter of the imaging receiver when the clearest image is collected.

Preferably, in a possible implementation manner of the embodiment of the present application, the optical parameter of the imaging receiver includes an optical axis direction of the imaging receiver.

Preferably, in a possible implementation manner of the embodiment of the present application, the method includes: when the imaging receiver is an eye, transfer an image presented on an eyeground to the image collection device respectively corresponding to the position of a pupil when an optical axis direction of the eye is different.

Preferably, in a possible implementation manner of the embodiment of the present application, before the step of collecting the image presented on the imaging plane of the imaging receiver, the method further includes: projecting a light spot to the imaging plane of the imaging receiver.

Preferably, in another possible implementation manner of the embodiment of the present application, the step of determining the focus position of the imaging receiver according to an optical parameter of the imaging receiver includes:

tracking an optical axis direction of the imaging receiver, then obtaining a scenario depth of the position of the observed object, and calculating the focus position of the imaging receiver.

Preferably, in yet another possible implementation manner of the embodiment of the present application, the method corresponds to at least two correlated imaging receivers, and the step of determining the focus position of the imaging receiver according to an optical parameter of the imaging receiver includes:

tracking optical axis directions of the at least two imaging receivers, and obtaining the focus position of the imaging receiver through an intersection of the optical axis directions of the at least two imaging receivers.

The specific implementation manner of the foregoing steps may be implemented according to the corresponding description of the apparatus embodiment, which is no longer described here.

A person skilled in the art may understand that in the method of the specific implementation manner of the present application, the sequence numbers of the steps do not mean a specific execution sequence, and the execution sequence of the steps should be determined based on the functions and internal logic thereof, rather to constitute any limitation on the implementation process of the specific implementation manner of the present application.

By means of the method of the present application, a user can see a clearest effect when watching a real scenario.

Persons of ordinary skill in the art may further appreciate that, in combination with the examples described in the embodiments herein, units and algorithm steps may be implemented by electronic hardware or a combination of computer software and electronic hardware. Whether these functions are performed using hardware or software depends on particular applications and design constraints of the technical solutions. A person skilled in the art may use different methods to implement the described functions for each specific application. However, such implementation should not be considered as beyond the scope of the present application.

If implemented in the form of software functional units and sold or used as an independent product, the functions may also be stored in a computer readable storage medium. Based on this, the above technical solution or the part that makes contributions to the prior art can be substantially embodied in the form of a software product. The computer software product may be stored in a storage medium and contain several instructions to instruct computer equipment (for example, a personal computer, a server, or network equipment) to perform all or a part of the steps of the method described in the embodiments of the present application. The storage medium may be any medium that is capable of storing program codes, such as a universal serial bus (USB) flash drive, a removable hard disk, a read-only memory (ROM), a RAM, a magnetic disk or an optical disk.

The above implementation manners are merely provided for describing the present invention, but not intended to limit the present invention. It should be understood by persons of ordinary skill in the art that various changes and variations can be made without departing from the spirit and scope of the present as defined by the claims of the present invention.

What is claimed is:

1. An apparatus, comprising:
a memory, coupled to a processor, that stores executable modules, comprising:
an imaging lens module comprising at least one adjustable imaging parameter, and used to image an observed object of an imaging receiver;
an information processing module used to detect a focus position of the imaging receiver, and determine the at least one adjustable imaging parameter of the imaging lens module according to the focus position; and
a lens adjustment module used to adjust the imaging lens module according to the at least one adjustable imaging parameter,
wherein the information processing module comprises:
a focus position determination unit used to determine an imaging receiver focus position of the imaging receiver according to at least one optical parameter of the imaging receiver,
wherein the focus position determination unit comprises:
a first focus position determination unit used to obtain the imaging receiver focus position of the imaging receiver according to at least one imaging parameter of at least one optical path between an image collection device and the imaging receiver in response to determining that a clearest image presented on an imaging plane of the imaging receiver has been collected by the image collection device, wherein the focus position of the imaging receiver comprises a distance between a focal point of the imaging receiver and the imaging receiver, and
wherein the first focus position determination unit comprises:
the image collection device used to collect an image presented on the imaging plane of the imaging receiver,
an adjustable lens unit used to adjust the at least one imaging parameter of the at least one optical path between the imaging receiver and the image collection device to enable the image collection device to obtain the clearest image, and
an image processing apparatus used to process the image obtained by the image collection device, and determine the focus position of the imaging receiver according to the at least one imaging parameter of the at least one optical path between the image collection device and the imaging receiver in response to determining that the image collection device has obtained the clearest image and the at least one optical parameter of the imaging receiver.

2. The apparatus of claim 1, wherein the information processing module comprises:
a refractive examination unit used to determine a corresponding imaging parameter of the at least one adjustable imaging parameter in response to acquisition by the imaging receiver of expected images of objects, comprising the observed object, at a plurality of distances, respectively, and obtain refractive examination information corresponding to the imaging receiver.

3. The apparatus of claim 2, wherein the imaging receiver comprises eyes.

4. The apparatus of claim 2, wherein the at least one optical parameter of the imaging receiver comprises an optical axis direction of the imaging receiver.

5. The apparatus of claim 2, wherein the adjustable lens unit is located on the at least one optical path between the imaging receiver and the image collection device, and has an adjustable focal length at an adjustable position in the at least one optical path.

6. The apparatus of claim 5, wherein the adjustable lens unit is continuously adjustable in real-time.

7. The apparatus of claim 2, further comprising:
a splitter apparatus used to form an optical transfer path between the imaging receiver and the observed object and between the imaging receiver and the image collection device.

8. The apparatus of claim 7, wherein the splitter apparatus comprises:
a curved surface splitter unit used to, in a case that the imaging receiver is an eye, transfer an image presented on an eyeground to the image collection device respectively corresponding to a position of a pupil in response to determining an optical axis direction of the eye has changed.

9. The apparatus of claim 2, wherein the first focus position determination unit further comprises:
a projection device used to project a light spot to the imaging plane of the imaging receiver.

10. The apparatus of claim 9, wherein the projection device comprises:
a projection control module that determines a brightness level of a projected light spot based on the focus position of the imaging receiver as determined by the image processing apparatus.

11. The apparatus of claim 10, wherein the brightness level of the projected light spot is adjustable by the projection control module based on the at least one imaging parameter as determined by the information processing module.

12. The apparatus of claim 1, wherein the focus position determination unit comprises:
a second focus position determination unit used to determine the focus position of the imaging receiver by tracking an optical axis direction of the imaging receiver with an optical axis tracking system and obtaining a scenario depth of a position of the observed object with a depth sensing device.

13. The apparatus of claim 1, wherein the apparatus corresponds to at least two correlated imaging receivers, and the focus position determination unit comprises:
a third focus position determination unit used to obtain the focus position of the imaging receiver by tracking optical axis directions of at least two imaging receivers with an optical axis tracking system and determining an intersection of the optical axis directions of the at least two imaging receivers.

14. The apparatus of claim 1, wherein the information processing module comprises:
an imaging parameter calculation unit used to determine the at least one imaging parameter of the imaging lens module according to the focus position of the imaging receiver and the refractive examination information corresponding to the imaging receiver.

15. The apparatus of claim 1, wherein the information processing module comprises:
a movement gesture analysis processing unit used to determine the at least one imaging parameter of the imaging lens module according to movement gesture information of the apparatus.

16. The apparatus of claim 15, wherein the movement gesture analysis processing unit comprises:
a movement trajectory prediction and adjustment subunit used to predict the at least one imaging parameter corresponding to the imaging lens module at a next moment according to relative movement gesture information of the apparatus and the observed object and the at least one imaging parameter of the imaging lens module at a current moment prior to the next moment.

17. The apparatus of claim 15, wherein the movement gesture analysis processing unit comprises:
a first movement adjustment subunit used to, in response to determining a movement speed of the apparatus has exceeded a set threshold value, adjust the at least one imaging parameter of the imaging lens module to a set common imaging parameter.

18. The apparatus of claim 15, wherein the movement gesture analysis processing unit comprises:
a second movement adjustment subunit used to, in response to determining a movement speed of the apparatus has exceeded a set threshold value, adjust the at least one imaging parameter of the imaging lens module to the at least one imaging parameter of the imaging lens module value at a moment previous to a current moment.

19. The apparatus of claim 15, further comprising:
a movement gesture sensing module used to acquire the movement gesture information of the apparatus.

20. The apparatus of claim 19, wherein the movement gesture information of the apparatus comprises at least one of relative movement gesture information of the apparatus and the observed object or movement speed information of the apparatus.

21. The apparatus of claim 1, wherein the information processing module further comprises:
a history information smoothing unit used to perform smoothing processing of time on a current value of an imaging parameter of the at least one imaging parameter of the imaging lens module according to history information of the imaging parameter of the imaging lens module.

22. The apparatus of claim 1, wherein the imaging lens module comprises at least one lens.

23. The apparatus of claim 1, wherein the imaging parameter of the imaging lens module comprises at least one of a shape and/or a refractive index of the imaging lens module.

24. The apparatus of claim 1, wherein the apparatus is glasses.

25. The apparatus of claim 1, wherein the adjustment to the imaging parameter of the imaging lens module comprises:
adjustment of a curvature of at least one surface of a lens of the imaging lens module to change the focal length of the imaging lens module.

26. The apparatus of claim 1, wherein the adjustment to the imaging parameter of the imaging lens module comprises:
adjustment of a refractive index of at least one surface of a lens of the imaging lens module to change the focal length of the imaging lens module.

* * * * *